(12) United States Patent
McEntire et al.

(10) Patent No.: US 11,738,122 B2
(45) Date of Patent: *Aug. 29, 2023

(54) ANTIBACTERIAL BIOMEDICAL IMPLANTS AND ASSOCIATED MATERIALS, APPARATUS, AND METHODS

(71) Applicant: SINTX Technologies, Inc., Salt Lake City, UT (US)

(72) Inventors: Bryan J. McEntire, Sandy, UT (US); Ramaswamy Lakshminarayanan, West Jordan, UT (US); Kevin Davis, Riverton, UT (US); Nicholas Grimaldi, Talbott, TN (US); Giuseppe Pezzotti, Kyoto (JP)

(73) Assignee: SINTX Technologies, Inc., Salt Lake City, UT (US)

(*) Notice: Subject to any disclaimer, the term of this patent is extended or adjusted under 35 U.S.C. 154(b) by 0 days.

This patent is subject to a terminal disclaimer.

(21) Appl. No.: 17/029,534

(22) Filed: Sep. 23, 2020

(65) Prior Publication Data
US 2021/0008254 A1    Jan. 14, 2021

Related U.S. Application Data

(63) Continuation of application No. 15/470,637, filed on Mar. 27, 2017, now Pat. No. 10,806,831, which is a
(Continued)

(51) Int. Cl.
*A61L 31/02*  (2006.01)
*A61L 31/16*  (2006.01)
(Continued)

(52) U.S. Cl.
CPC ............ *A61L 31/028* (2013.01); *A61L 27/06* (2013.01); *A61L 27/306* (2013.01); *A61L 27/50* (2013.01);
(Continued)

(58) Field of Classification Search
CPC .......... B23B 3/26; A61L 31/028; A61L 27/06; A61L 27/02; A61C 8/00
See application file for complete search history.

(56) References Cited

U.S. PATENT DOCUMENTS 6,302,913 B1 * 10/2001 Ripamonti ............. A61L 27/12
623/23.76
10,563,302 B1    2/2020 Dacus et al.
(Continued)

FOREIGN PATENT DOCUMENTS

JP    2015216239 A    6/2015
JP    2015516239 A    6/2015
(Continued)

OTHER PUBLICATIONS

Olofsson et al., Evaluation of silicon nitride as a wear resistant and resorbable alternative for total hip joint replacement, Apr. 1, 2012, Biomatter, vol. 2, No. 2, pp. 94-102 (Year: 2012).*
(Continued)

*Primary Examiner* — Dah-Wei D. Yuan
*Assistant Examiner* — Andrew J Bowman
(74) *Attorney, Agent, or Firm* — Polsinelli PC

(57) ABSTRACT

Methods for improving the antibacterial characteristics of biomedical implants and related implants manufactured according to such methods. In some implementations, a biomedical implant comprising a silicon nitride ceramic material may be subjected to a surface roughening treatment so as to increase a surface roughness of at least a portion of the biomedical implant to a roughness profile having an arithmetic average of at least about 500 nm Ra. In some implementations, a coating may be applied to a biomedical implant. Such a coating may comprise a silicon nitride ceramic material, and may be applied instead of, or in addition to, the surface roughening treatment process.

14 Claims, 13 Drawing Sheets

Related U.S. Application Data continuation-in-part of application No. 13/890,876, filed on May 9, 2013, now abandoned.

(60) Provisional application No. 61/644,906, filed on May 9, 2012.

(51) Int. Cl.

| | | |
|---|---|---|
| *A61L 31/12* | (2006.01) | |
| *A61L 31/08* | (2006.01) | |
| *A61L 27/30* | (2006.01) | |
| *A61L 31/14* | (2006.01) | |
| *A61L 27/50* | (2006.01) | |
| *A61L 27/06* | (2006.01) | |

(52) U.S. Cl.
CPC .......... *A61L 31/022* (2013.01); *A61L 31/026* (2013.01); *A61L 31/088* (2013.01); *A61L 31/12* (2013.01); *A61L 31/14* (2013.01); *A61L 31/16* (2013.01); *A61L 2300/10* (2013.01); *A61L 2300/406* (2013.01); *A61L 2400/18* (2013.01); *A61L 2430/02* (2013.01); *A61L 2430/38* (2013.01)

(56) References Cited

U.S. PATENT DOCUMENTS

| | | | | |
|---|---|---|---|---|
| 2006/0276788 | A1* | 12/2006 | Berry | A61B 17/866 606/301 |
| 2011/0189466 | A1* | 8/2011 | Jaggi | C23C 4/06 427/446 |
| 2013/0090733 | A1* | 4/2013 | Kraft | A61F 2/442 623/17.16 |
| 2013/0302509 | A1* | 11/2013 | McEntire | A61L 27/025 427/2.24 |
| 2016/0339144 | A1* | 11/2016 | McEntire | A61L 27/446 |
| 2020/0337860 | A1 | 10/2020 | Kuyler et al. | |

FOREIGN PATENT DOCUMENTS

| | | | | |
|---|---|---|---|---|
| KR | 1020110057691 A | 6/2011 | | |
| WO | 2010007424 A | 1/2010 | | |
| WO | 2013030787 A1 | 3/2013 | | |
| WO | WO2013/030787 | * | 3/2013 | ............. A61L 27/30 |
| WO | 2017027426 A1 | 2/2017 | | |

OTHER PUBLICATIONS

Office Action issued is corresponding Canadian Application No. 3,055,721 dated Jul. 14, 2021, 4 pages.
Official Action issued is corresponding Canadian Application No. 3,055,721 dated Nov. 27, 2020, 4 pages.
Extended European Search Report in corresponding Application No. 18774889.2 dated Nov. 5, 2020, 8 pages.
Hu, et a., A microporous surface containing Si3N4/Ta microparticles of PEKK exhibits both antibacterial and osteogenic activity for inducing cellular response and improving osseointegration, Bioactive Materials 6 (2021) 3136-3149, 2021.
Office Action issued in corresponding Japanese Application No. 2019-549564 dated Sep. 1, 2020, 5 pages.
Examination Report No. 1 for corresponding Australian Application No. 2020286172 dated Nov. 29, 2021, 6 pages.
Office Action for corresponding Chinese Application No. 201880021458.2 dated Nov. 11, 2021, 15 pages.
Reconsideration Report dated Feb. 25, 2022 in corresponding Japanese Application No. 2019-549564, 1 page.
Preliminary Office Action dated Apr. 28, 2022 in corresponding Brazilian Application No. BR112019018892-4, 7 pages.
English translation of Notice of Reasons for Rejection issued in related Japanese Application No. 2020-199903 dated Feb. 17, 2022, 4 pages.
Korean Office Action dated May 31, 2022 in corresponding Application No. 10-2019-7026376, 11 pages.
Korean Intellectual Property Office, Notification of Provisional Rejection, Application No. 10-2019-7026376, dated Dec. 29, 2022, 11 pages.
Wang, Q. et al., "An investigation of the friction and wear properties of nanometer Si3N4 filled PEEK", 1996, WEAR, vol. 196, 1996, pp. 82-86.
Office Action dated Oct. 6, 2022 in Brazilian Patent Application No. BR112019018892-4, 6 pages.
European Patent Office, Extended European Search Report, Application No. 22212616.1, dated Apr. 13, 2023, 7 pages.

\* cited by examiner

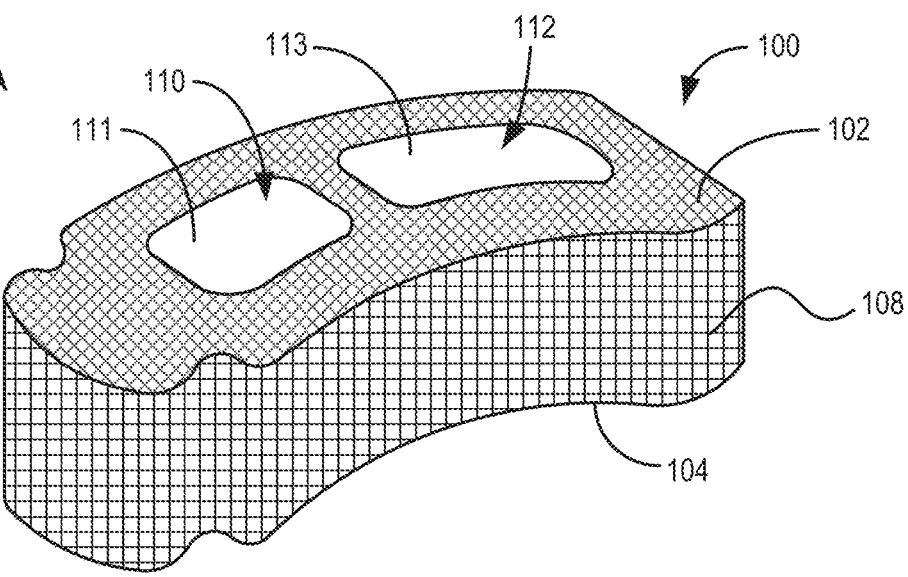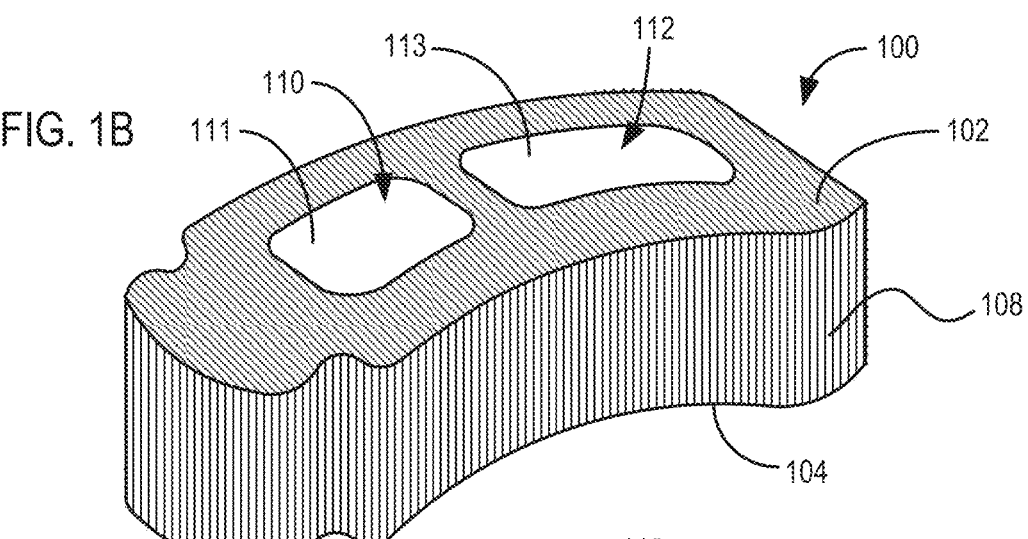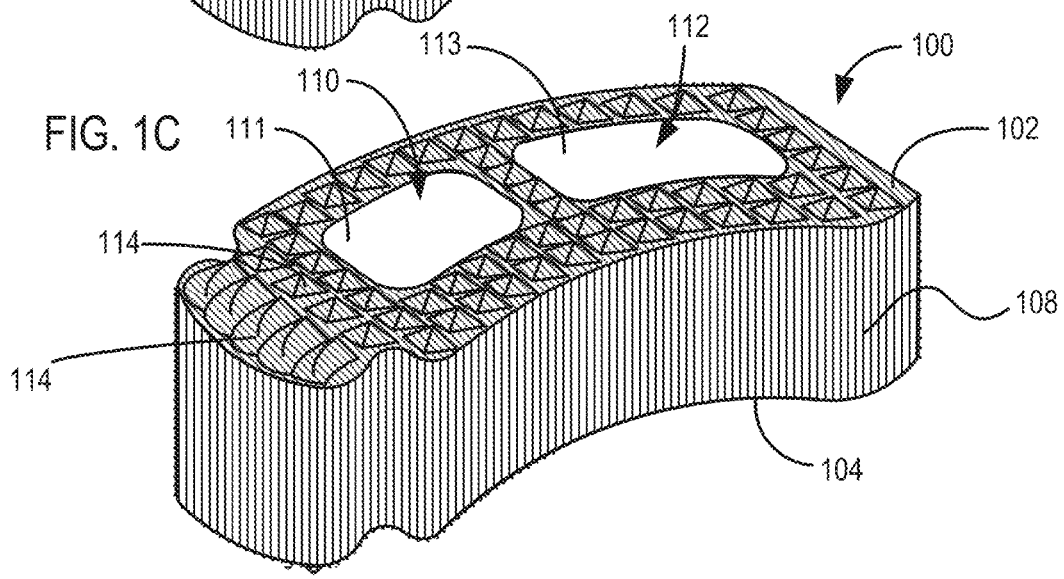

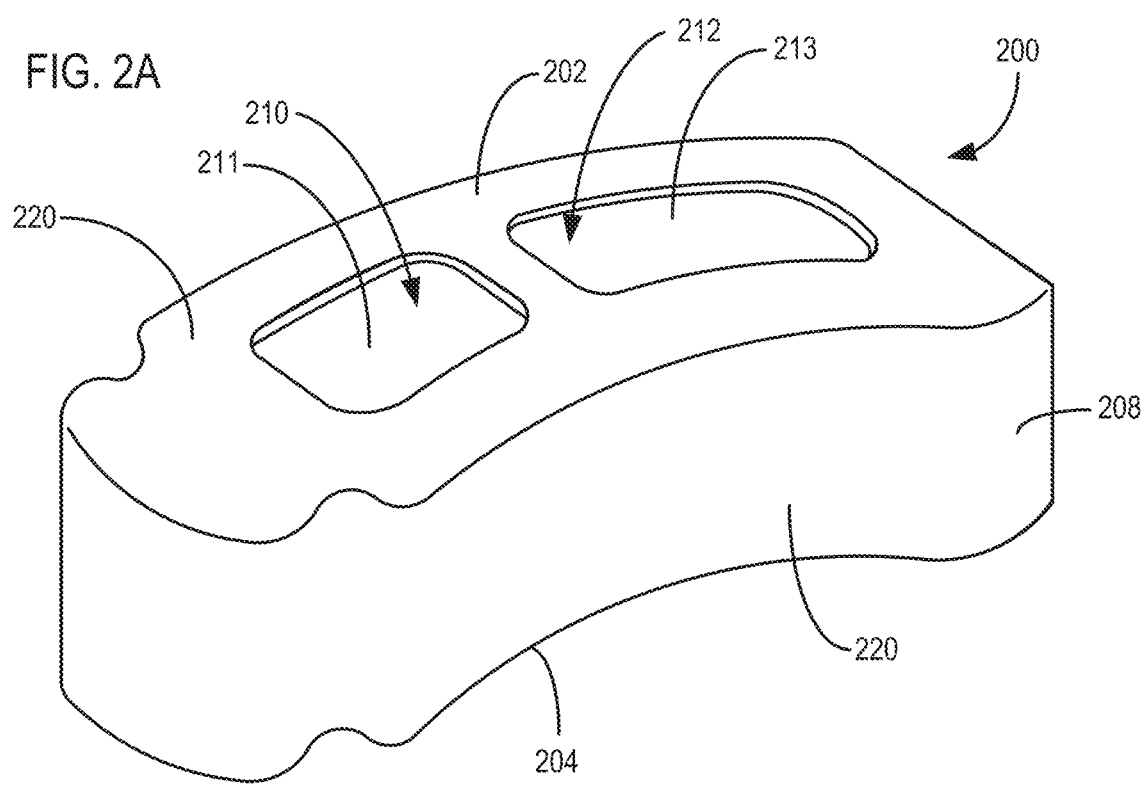
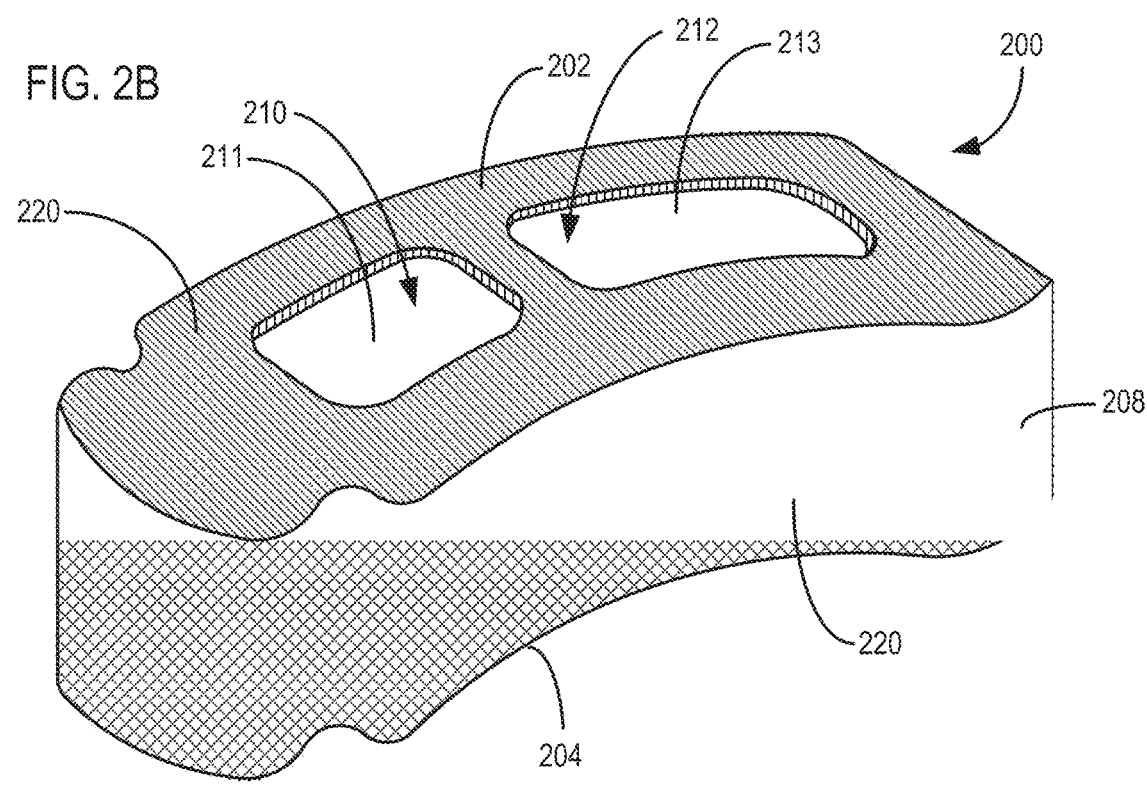

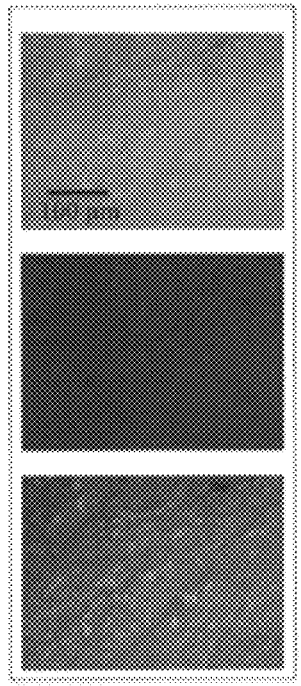 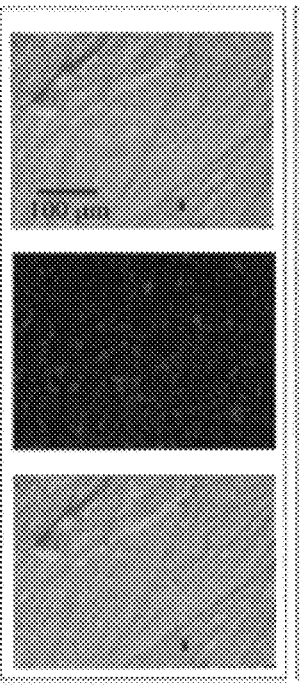 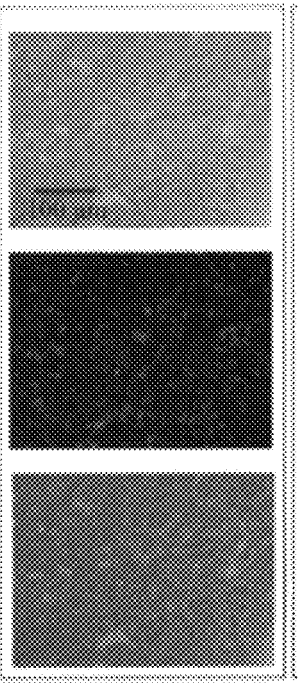 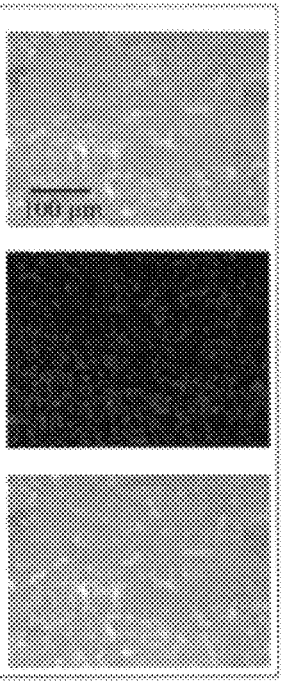
FIG. 6A PEEK  FIG. 6B PEEK+α-Si₃N₄  FIG. 6C PEEK+β-Si₃N₄  FIG. 6D PEEK+β-SiYAlON FIG. 8A  
PEEK
FIG. 8B  
PEEK + α-Si$_3$N$_4$
FIG. 8C  
PEEK + β-Si$_3$N$_4$
FIG. 8D  
PEEK + β-SiYAlON
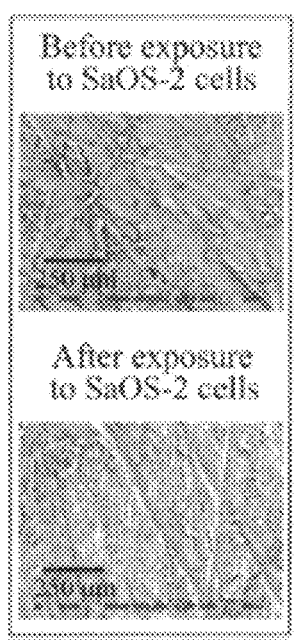
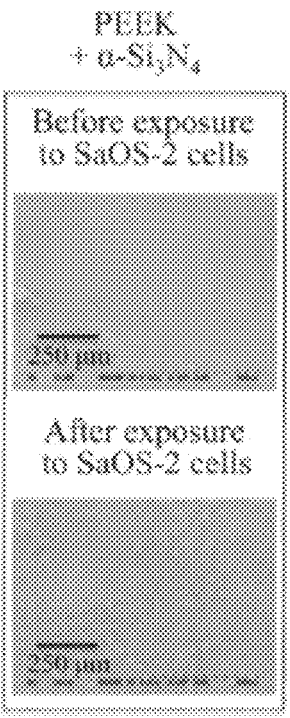
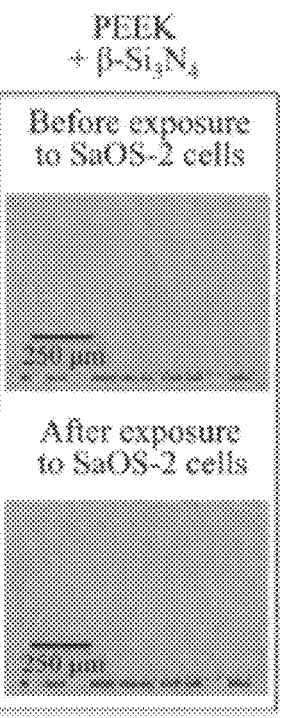
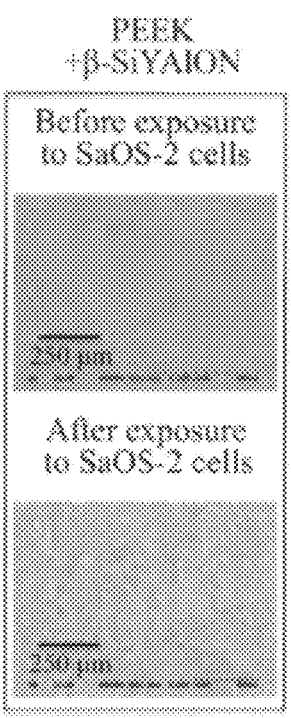

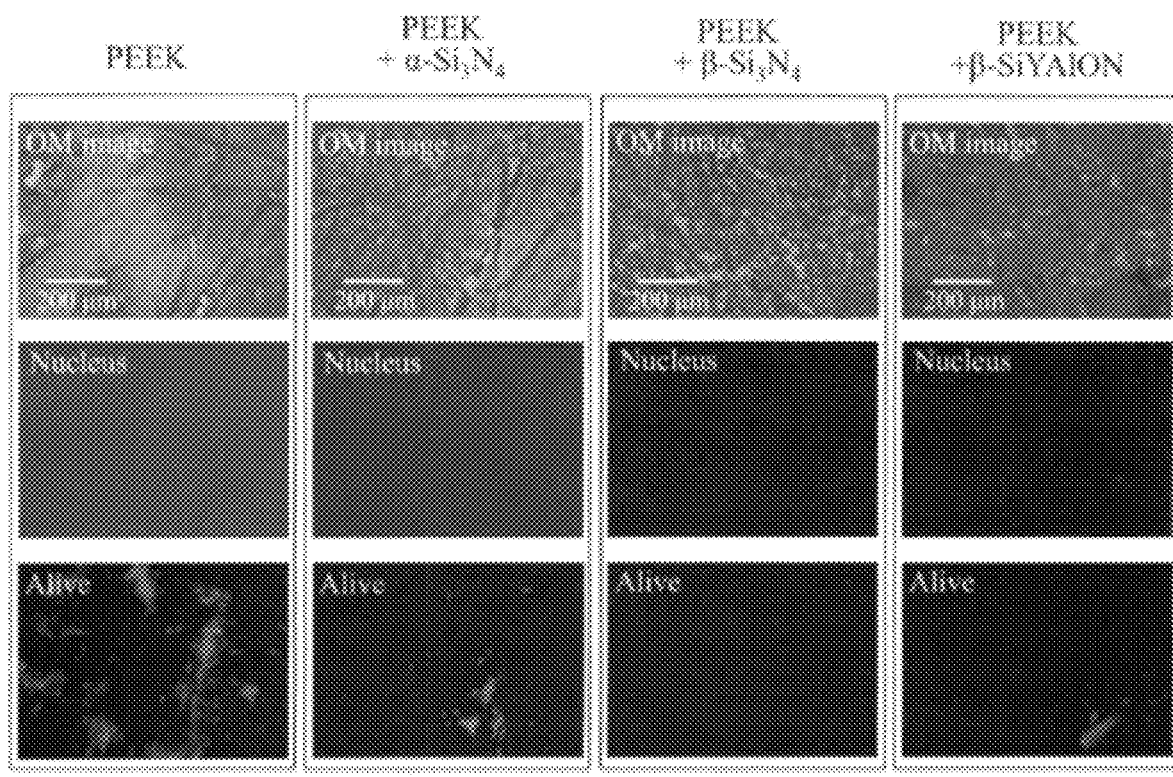

ANTIBACTERIAL BIOMEDICAL IMPLANTS AND ASSOCIATED MATERIALS, APPARATUS, AND METHODS

CROSS REFERENCE TO RELATED APPLICATIONS

This application is a continuation application of Ser. No. 15/470,637 filed Mar. 27, 2017 that is a Continuation-In-Part to U.S. Non-Provisional application Ser. No. 13/890,876, filed on May 9, 2013, which claims benefit to U.S. Provisional Patent Application No. 61/644,906 filed May 9, 2012, which are herein incorporated herein by reference in their entirety.

FIELD

The present disclosure generally relates to antibacterial biomedical implants, and in particular to materials, apparatuses and methods for improving the antibacterial characteristics of an intervertebral spinal implant.

BACKGROUND

Polymeric materials are poor at both osteointegration and microbial resistance. Prior work to overcome this involves inclusion of either an antimicrobial or osteogenic materials onto or into the polymeric material. In these cases, hydroxyapatite is typically cited as the material that improves osteoconduction, whereas the antimicrobial compound is typically silver or an antibiotic. However, there is a need for the improvement of the osteogenic and anti-infective properties of the polymeric material using one material.

It is with these observations in mind, among others, that various aspects of the present disclosure were conceived and developed.

SUMMARY

A need exists for an improved biomedical implant with antibacterial properties. Accordingly, one embodiment of the present disclosure may include a method for improving the antibacterial characteristics of a biomedical implant. The method may include the steps of: providing a biomedical implant; and loading the biomedical implant with about 10% to about 20% of a powder, wherein the powder comprises a silicon nitride material. The method may further include increasing a surface roughness of at least a portion of the biomedical implant to a roughness profile having an arithmetic average of at least about 500 nm Ra to improve the antibacterial characteristics of the biomedical implant by at least one of micromachining, grinding, polishing, laser etching, laser texturing, sand- or other abrasive-blasting, chemical etching, thermal etching, and plasma etching. The silicon nitride material may be selected from the group consisting of $\alpha$-$Si_3N_4$, $\beta$-$Si_3N_4$, $\beta$-SiYAlON, and combinations thereof. The biomedical implant may be an intervertebral spinal implant. The biomedical implant may include poly-ether-ether-ketone (PEEK), titanium, PEEK and $\beta$-$Si_3N_4$ powder, or PEEK and $\beta$-SiYAlON powder.

In other embodiments, the method may further include applying a coating of silicon nitride to the biomedical implant. The step of increasing a surface roughness of at least a portion of the biomedical implant may be performed after the step of applying a coating to the biomedical implant, and the step of increasing a surface roughness of at least a portion of the biomedical implant may include increasing a surface roughness of at least a portion of the coating. The step of increasing a surface roughness of at least a portion of the biomedical implant to a roughness profile having an arithmetic average of at least about 1,250 nm Ra or between about 2,000 nm Ra and about 5,000 nm Ra.

Another implementation of the present disclosure may take the form of a biomedical implant with improved antibacterial characteristics. The biomedical implant may include a polymeric or metallic substrate material; and about 10% to about 20% of a powder, wherein the powder comprises a silicon nitride material. At least a portion of the implant may have an increased surface roughness profile having an arithmetic average of at least about 500 nm Ra created by at least one of micromachining, grinding, polishing, laser etching, laser texturing, sand- or other abrasive-blasting, chemical etching, thermal etching, and plasma etching. The silicon nitride material may be selected from the group consisting of $\alpha$-$Si_3N_4$, $\beta$-$Si_3N_4$, $\beta$-SiYAlON, and combinations thereof. The substrate material may include poly-ether-ether-ketone (PEEK), titanium, PEEK $\beta$-$Si_3N_4$ powder, or PEEK and 15% $\beta$-SiYAlON powder. The biomedical implant may be an intervertebral spinal implant, a hip implant, or a bone screw. The biomedical implant may include a hip implant with a silicon nitride coating on a femoral stem of the hip implant. The biomedical implant may further include a silicon nitride coating on the biomedical implant.

BRIEF DESCRIPTION OF THE DRAWINGS

The written disclosure herein describes illustrative embodiments that are non-limiting and non-exhaustive. Reference is made to certain of such illustrative embodiments that are depicted in the figures, in which:

FIG. 1A is a perspective view of one embodiment of a spinal implant; FIG. 1B is a perspective view of the spinal implant of FIG. 1A after a surface roughening process has been applied to the implant; and FIG. 1C is a perspective view of the spinal implant of FIG. 1B with surface features for minimizing implant migration, according to one aspect of the present disclosure;

FIG. 2A is a perspective view of another embodiment of a spinal implant having a coating applied thereto; and FIG. 2B is a perspective view of the embodiment of FIG. 2A after a surface roughening process has been applied to the coating of the implant, according to one aspect of the present disclosure;

FIG. 6A shows fluorescence spectroscopy images of SaOS-2 cells on monolithic PEEK; FIG. 6B shows fluorescence spectroscopy images of SaOS-2 cells on PEEK with 15% $\alpha$-$Si_3N_4$; FIG. 6C shows fluorescence spectroscopy images of SaOS-2 cells on PEEK with 15% $\beta$-$Si_3N_4$; and FIG. 6D shows fluorescence spectroscopy images of SaOS-2 cells on PEEK with 15% β-SiYAlON, according to one aspect of the present disclosure;

FIG. 8A shows SEM images of monolithic PEEK before and after exposure to the SaOS-2 cells; FIG. 8B shows SEM images of PEEK with 15% α-$Si_3N_4$ before and after exposure to the SaOS-2 cells; FIG. 8C shows SEM images of PEEK with 15% β-$Si_3N_4$ before and after exposure to the SaOS-2 cells; and FIG. 8D shows SEM images of PEEK with 15% β-SiYAlON before and after exposure to the SaOS-2 cells, according to one aspect of the present disclosure;

FIG. 11A shows fluorescence microscopy images with DAPI/CFDA staining of *S. epidermis* on monolithic PEEK; FIG. 11B shows fluorescence microscopy images with DAPI/CFDA staining of *S. epidermis* on PEEK with 15% α-$Si_3N_4$; FIG. 11C shows fluorescence microscopy images with DAPI/CFDA staining of *S. epidermis* on PEEK with 15% β-$Si_3N_4$; and FIG. 11D shows fluorescence microscopy images with DAPI/CFDA staining of *S. epidermis* on PEEK with 15% β-SiYAlON, according to one aspect of the present disclosure.

DETAILED DESCRIPTION

Figure 3A:
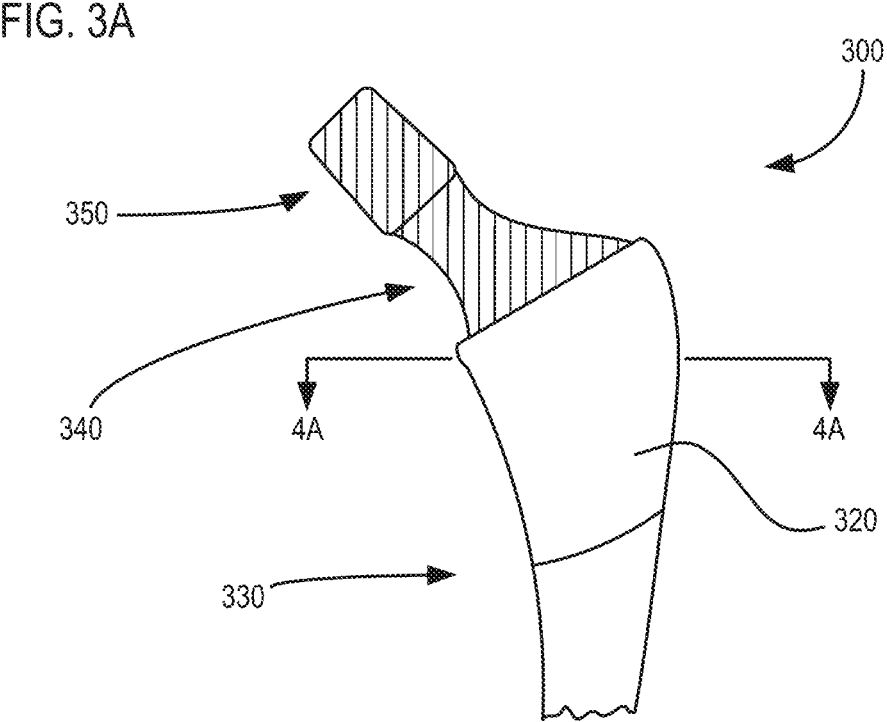
FIG. 3A is a perspective view of an embodiment of a hip stem implant having a coating applied to a portion of the implant.

Embodiments described herein may be best understood by reference to the drawings, wherein like parts are designated by like numerals throughout. It will be readily understood that the components of the present disclosure, as generally described and illustrated in the drawings herein, could be arranged and designed in a wide variety of different configurations. Thus, the following more detailed description of the embodiments of the apparatus is not intended to limit the scope of the disclosure, but is merely representative of possible embodiments of the disclosure. In some cases, well-known structures, materials, or operations are not shown or described in detail.

Various embodiments of apparatus, methods, and systems are disclosed herein that relate to biomedical implants having antibacterial characteristics and materials and methods for improving the antibacterial function and/or characteristics of such implants. In preferred embodiments, silicon nitride ceramic implants are provided that may be, in some embodiments, treated so as to improve upon their antibacterial characteristics and/or other desirable characteristics. For example, embodiments and implementations disclosed herein may result in improved inhibition of bacteria adsorption and biofilm formation, improved protein adsorption, and/or enhanced osteoconductive and osteointegration characteristics. Such embodiments may comprise a silicon nitride ceramic or doped silicon nitride ceramic substrate. Alternatively, such embodiments may comprise a silicon nitride or doped silicon nitride coating on a substrate of a different material. In other embodiments, the implant and the coating may be made up of a silicon nitride material. In still other embodiments, one or more portions or regions of an implant may include a silicon nitride material and/or a silicon nitride coating, and other portions or regions may include other biomedical materials.

As another alternative, silicon nitride or other similar ceramic materials may be incorporated into other materials used to form biomedical implants. For example, silicon nitride may be used as a filler or otherwise incorporated into polymers or biodegradable polymers, such as poly-ether-ether-ketone (PEEK), poly(methyl methacrylate), poly(ethylene terephthalate), poly(dimethylsiloxane), poly(tetrafluoroethylene), polyacrylic acids, polylactic acids, polycarbonates, polyethylene, and/or polyurethane, in their porous scaffolds or bulk structures. In some embodiments, the silicon nitride filler may be β-silicon nitride and may be present in the biomedical implant in amounts ranging from about 1 wt. % to about 99 wt. %. For example a β-silicon powder may be incorporated into a PEEK biomedical implant in an amount from about 10 wt % to about 20 wt. %. Silicon nitride may also be used as a filler otherwise incorporated into other materials used to form other biomedical implants, such as metals, including Titanium, Silver, Nitinol, Platinum, Copper, Cobalt/Chromium, and related alloys, for example. As still another alternative, silicon nitride may be used as a filler or otherwise incorporated into other materials, such as ceramics and cermets.

In embodiments including one or more coatings, the coating(s) can be applied by any number of methods such as chemical vapor deposition (CVD), physical vapor deposition (PVD), plasma spraying, electro-deposition or electrophoretic deposition, slurry coating and high-temperature diffusion, or any other application method known by those skilled in the art. In some embodiments, the coating thickness can range from between about 5 nanometers up to about 5 millimeters. In some such embodiments, the coating thickness may be between about 1 micrometer and about 125 micrometers. The coating may adhere to the surface of the implant, but need not necessarily be hermetic.

Silicon nitride ceramics have tremendous flexural strength and fracture toughness. In some embodiments, such ceramics have been found to have a flexural strength greater than about 700 Mega-Pascal (MPa). Indeed, in some embodiments, the flexural strength of such ceramics have been measured at greater than about 800 MPa, greater than about 900 MPa, or about 1,000 MPa. The fracture toughness of silicon nitride ceramics in some embodiments exceeds about 7 Mega-Pascal root meter (MPa·m$^{1/2}$). Indeed, the fracture toughness of such materials in some embodiments is about 7-10 MPa·m$^{1/2}$.

Examples of suitable silicon nitride materials are described in, for example, U.S. Pat. No. 6,881,229, titled "Metal-Ceramic Composite Articulation," which is incorporated by reference herein. In some embodiments, dopants such as alumina ($Al_2O_3$), yttria ($Y_2O_3$), magnesium oxide (MgO), and strontium oxide (SrO), can be processed to form a doped composition of silicon nitride. In embodiments comprising a doped silicon nitride or another similar ceramic material, the dopant amount may be optimized to achieve the highest density, mechanical, and/or antibacterial properties. In further embodiments, the biocompatible ceramic may have a flexural strength greater than about 900 MPa, and a toughness greater than about 9 MPa·m$^{1/2}$. Flexural strength can be measured on standard 3-point bend specimens per American Society for Testing of Metals (ASTM) protocol method C-1161, and fracture toughness can be measured using single edge notched beam specimens per ASTM protocol method E399. In some embodiments, powders of silicon nitride may be used to form the ceramic implants, either alone or in combination with one or more of the dopants referenced above.

Other examples of suitable silicon nitride materials are described in U.S. Pat. No. 7,666,229 titled "Ceramic-Ceramic Articulation Surface Implants," which is hereby incorporated by reference. Still other examples of suitable silicon nitride materials are described in U.S. Pat. No. 7,695,521 titled "Hip Prosthesis with Monoblock Ceramic Acetabular Cup," which is also hereby incorporated by reference.

Silicon nitride has been discovered to have unexpected antibacterial properties and increased bone formation properties. Indeed, as discussed in greater detail below, it has been recently demonstrated that the adhesion and growth of bacteria on silicon nitride materials is substantially reduced with respect to other common spinal implant materials, such as Titanium and polyetheretherketone (PEEK). As discussed in greater detail below, compared to medical grade titanium and PEEK, silicon nitride significantly inhibits in vitro and in vivo bacteria colonization, and bio-film formation. Silicon nitride also exhibits a much lower live count and live to dead ratio for bacteria during studies.

It has also been demonstrated that silicon nitride materials provide significantly greater adsorption of vitronectin and fibronectin, which proteins are known to decrease bacteria function, than Titanium and PEEK. It is thought that these properties will be very useful in biomedical implants of all types by significantly reducing the possibility of infection. This may be accomplished by, for example, preventing or disrupting bacterial formation on/in the implant and/or killing bacteria that have been transferred to the implant.

Without being limited by theory, it is thought that the higher adsorption of proteins that characterizes silicon nitride may facilitate the inhibition of bacteria growth and promote stem cell differentiation to osteoblasts. This preferential adsorption may be a cause for silicon nitride's ability to decrease bacteria function. Again, without being limited by theory, the mechanisms for the enhanced antibacterial characteristics of silicon nitride may be a combination of its features. For example, its hydrophilic surface may lead to preferential adsorption of proteins that are responsible for reduced bacteria function. This effect may be enhanced by increasing the surface texture or roughness of a silicon nitride based implant or silicon nitride based coating on an implant made up of a different material. Because of these characteristics, silicon nitride also exhibits enhanced in vivo osteoconduction and osteointegration when compared with titanium or PEEK alone.

As discussed above, using a silicon nitride coating or filler on one or more regions of an implant's surface may be used, in some embodiments and implementations, to inhibit bacterial adhesion, while increasing/fostering adsorption of proteins necessary for healing and bone reformation. This same effect may, in other embodiments, be accomplished using monolithic silicon nitride as an implant.

In such embodiments, the surface of the ceramic implant may be engineered to provide for an increased degree of micro-roughness and surface texture to enhance these desirable properties. For example, in some embodiments, the micro-roughness—i.e., the texture of the surface in between the peaks and valleys typically measured by Ra values—may also, or alternatively, be increased by suitable texturing. In some implementations, the micro-roughness of the implant and/or coating may be increased by micromachining, grinding, polishing, laser etching or texturing, sand- or other abrasive-blasting, chemical, thermal or plasma etching, and the like. Micro-roughness may be measured by measuring the height of surface asperities using cut-off limits on a profilometer. This method may be used to selectively assess the roughness of a surface between the peaks and valleys. Alternatively, or additionally, the skewness and/or kurtosis could be measured. These measurements consider the deviation of the surface from what might be expected of a normal Gaussian distribution of surface roughness. Such surface engineering may also be performed on a silicon nitride coating, rather than on a monolithic silicon nitride or silicon nitride composite implant.

In some embodiments, the density of the silicon nitride material, or doped silicon nitride material, may vary throughout the implant, or throughout the portion of the implant made up of silicon nitride. For example, in spinal implant embodiments, the outermost layer, or a portion of the outermost layer, may be more porous, or less dense, than the core or center of the implant. This may allow for bone to grow into or otherwise fuse with a less dense portion of the implant, and the denser portion of the implant can be wear-resistant, and may have a higher strength and/or toughness, for example.

In certain embodiments, one or more inner portions of the implant may have a relatively low porosity or non-porous ceramic, and thus exhibit high density and high structural integrity generally consistent with, and generally mimicking the characteristics of, natural cortical bone. And, by contrast, one or more of the surface coatings, layers, or linings formed at an outer surface of the implant can exhibit a comparatively greater or higher porosity that is generally consistent with and generally mimics the characteristics of natural cancellous bone. As a result, the higher porosity surface region(s), coating(s), or lining(s) can provide an effective bone ingrowth surface for achieving secure and stable bone ingrowth affixation of the ceramic portion of the implant (which, in some embodiments, comprises the entire implant) between a patient's vertebrae or another suitable location within the human body.

In some embodiments, the antibacterial behavior of other implant materials, such as polymeric, metallic, or ceramics, may be improved through the application of silicon nitride as an adherent coating. This coating may, in some implementations, be roughened or textured to provide for increased surface area of the silicon nitride material/coating. In other embodiments, monolithic silicon nitride implantable devices may be provided which may be subjected to similar surface engineering.

The surface roughness values disclosed herein may be calculated using the arithmetic average of the roughness profile (Ra). Polished silicon nitride surfaces may have a roughness of 20 nm Ra or less. However, as discussed in greater detail below, counterintuitively, the antibacterial properties of certain embodiments may be improved by roughening, rather than polishing, all or one or more portions of the surface of a silicon nitride ceramic or another similar ceramic implant. In some embodiments, a relatively rough surface may be created as part of the process of creating the material, such as during a firing stage, without further roughening or other surface engineering. However, in other embodiments, as discussed in greater detail below, the surface may be roughened to further increase the roughness beyond what would occur as a result of standard firing/curing alone. Thus, in some embodiments, the surface roughness may be greater than about 1,250 nm Ra. In some such embodiments, the surface roughness may be greater than about 1,500 nm Ra. In some such embodiments, the surface roughness may be greater than about 2,000 nm Ra. In some such embodiments, the surface roughness may be greater than about 3,000 nm Ra. In other embodiments, the surface roughness may be between about 500 nm Ra and about 5,000 nm Ra. In some such embodiments, the surface roughness may be between about 1,500 nm Ra and about 5,000 nm Ra. In some such embodiments, the surface roughness may be between about 2,000 nm Ra and about 5,000 nm Ra. In some such embodiments, the surface roughness may be between about 3,000 nm Ra and about 5,000 nm Ra.

In certain embodiments, metallic, polymeric, or ceramic implant substrates may be filled with a silicon nitride powder. Non-limiting examples of filler silicon nitride powders include $\alpha$-$Si_3N_4$, $\beta$-$Si_3N_4$, and $\beta$-SiYAlON powders. Non-limiting examples of metallic or polymeric biomedical implant substrates that may be filled with silicon nitride powder include poly-ether-ether-ketone (PEEK), poly(methylmethacrylate), poly(ethyleneterephthalate), poly(dimethylsiloxane), poly(tetrafluoroethylene), polyacrylic acids, polylactic acids, polycarbonates, polyethylene, polyurethane, Titanium, Silver, Nitinol, Platinum, Copper, and/or related alloys. In various embodiments, a PEEK implant may be filled with $\beta$-$Si_3N_4$ or 13-SiYAlON ground powders. The percentage of ground silicon nitride powder in the implant may range from about 1 wt. % to about 99 wt. %. In various aspects, the silicon nitride in the implant may range from about 1 wt. % to about 5 wt. %, from about 5 wt. % to about 15 wt. %, from about 10 wt. % to about 20 wt. %, from about 15 wt. % to about 25 wt. %, from about 20 wt. % to about 30 wt. %, from about 25 wt. % to about 35 wt. %, from about 30 wt. % to about 50 wt. %, from about 40 wt. % to about 60 wt. %, from about 50 wt. % to about 70 wt. %, from about 60 wt. % to about 80 wt. %, from about 70 wt. % to about 90 wt. %, and from about 80 wt. % to about 99 wt. %. In one embodiment, a PEEK implant may include up to about 15% $\beta$-$Si_3N_4$ or $\beta$-SiYAlON.

In an embodiment, the SiYAlON and $\beta$-$Si_3N_4$ materials may have added aluminum-oxide and yttrium-oxide. Without being limited to a particular theory, the functional surface chemistry of the implant may be enhanced by the additions of these oxide dopants.

In some embodiments, a polymeric implant filled with silicon nitride powder may improve the osteoconductivity and antibacterial activity of the implant compared to the implant without the silicon nitride filler. For example, a PEEK implant filled with $\beta$-$Si_3N_4$ or $\beta$-SiYAlON may improve osteoconductivity and antibacterial characteristics of the implant compared to a monolithic PEEK implant. In an embodiment, the surface of the implant filled with silicon nitride powder may further be modified with a surface roughness and may or may not further include a silicon nitride coating. Some of the methods disclosed herein may therefore provide for engineering of the surface roughness of silicon nitride ceramic filled implants in order to improve their antibacterial performance.

Without being limited to a particular theory, the addition of a relatively low fraction of $\beta$-$Si_3N_4$ or $\beta$-SiYAlON or a suitable mixture thereof may enhance in vitro osteoconductivity and antibacterial resistance of PEEK. The silicon nitride filled PEEK implants have substantially better results than other substrates without a silicon nitride filler. It was unexpected that a PEEK implant filled with $\alpha$-$Si_3N_4$ exhibited an increased osteoconductivity and reduced antibacterial resistance while 13-$Si_3N_4$ or $\beta$-SiYAlON had both an increased osteoconductivity and antibacterial resistance.

In some embodiments, metallic, polymeric, or ceramic substrates may be pre-engineered with a surface texture onto which a silicon nitride coating may be applied. This texture can range from as low as about 5 nanometers up to about 5,000 nanometers or more in average surface roughness (Ra). Alternatively, as another embodiment, the surface texture of the silicon nitride coating itself can be increased, exclusive of the surface roughness of the substrate, to obtain a similar Ra range and resulting antibacterial effect. Some of the methods disclosed herein may therefore provide for engineering of the surface roughness of monolithic silicon nitride ceramic implants in order to improve their antibacterial performance, and other methods disclosed herein may provide for engineering the surface roughness of layers or coatings applied to substrates made up of any other suitable material available for use in biomedical implants. Of course, in some implementations, surface engineering may be applied to both the substrate and the coating.

Increasing the surface roughness of the ceramic or ceramic filled implant can be accomplished using any number of known methods by those skilled in the art, including micromachining, grinding, polishing, laser etching or texturing, sand or other abrasive blasting, chemical etching, thermal etching, plasma etching, and the like.

The inventive techniques disclosed herein, including but not limited to the silicon nitride coatings and roughened surface finishes, may be applied to any number and type of biomedical components including, without limitation, spinal cages, orthopedic screws, plates, wires, and other fixation devices, articulation devices in the spine, hip, knee, shoulder, ankle and phalanges, catheters, artificial blood vessels and shunts, implants for facial or other reconstructive plastic surgery, middle ear implants, dental devices, and the like.

As illustrated in the Examples presented below, in comparison with titanium and poly-ether-ether-ketone (PEEK), silicon nitride significantly inhibits in vitro and in vivo bio-film formation and bacterial colonization, and shows much lower bacteria live/dead ratios for bacteria, including but not limited to *Staphylococcus epidermidis* (*Staph. Epi.*), *Staphylococcus aureus* (*Staph. aureus*), *Enterococcus*, *Pseudomonas aeruginosa* (*Pseudo. aeruginosa*), and *Escherichia Coli* (*E. coli*). Silicon nitride also demonstrates significantly higher in vitro adsorption of three proteins (Fibronectin, Vitronectin, and Laminin) which can displace or inhibit bacteria growth and promote stem cell differentiation to osteoblasts.

In a clinical setting, bacteria are an ever present menace, particularly when associated with surgical intervention and the introduction of foreign material into the human body, such as orthopedic, cardiac or dental endoprostheses. Microorganisms introduced during surgery tend to initially populate the sterile surfaces of implants. Bacterial adhesion to the biomaterial surface is the essential step in the development of an infection. The human body's defensive mechanisms are triggered if the implant is excessively colonized by bacteria. Chronic infections arise when the bacterial colony reaches a critical size and overcomes the local host defenses. When this occurs, the body tends to encapsulate the infection and reject the implant. Consequently, patients typically must undergo re-operation, removal of the implant, treatment of the infection, and replacement of the implant. Deep wound infections associated with common orthopedic surgeries can be as high as 4% and cost up to $100,000 or more for corrective treatment. The reduction in quality of life and the associated cost of treating infections represents a significant burden for present day medical care.

Various embodiments and implementations disclosed herein will therefore provide materials and methods that resist bacterial adhesion, colonization, and growth, which, as discussed above, often lead to chronic infections. The embodiments and implementations disclosed herein may also provide for enhanced in vivo osteointegration and increased bone growth in comparison to other common implants, such as those made up of only Titanium and PEEK.

Factors influencing bacteria adhesion to biomaterial surfaces may include chemical composition, surface charge, hydrophobicity, and surface roughness or physical characteristics of the surface and/or coating of an implant. There are marked differences in the surface chemistry of metallic, polymeric, and ceramic implants. Metals typically have a thin protective oxide layer on their surfaces (typically less than about 25 nm in thickness). Polymers may also have oxide surfaces, but the oxides are typically part of longer chain carboxyl or hydroxyl groups. Both metallic and polymeric surfaces are often low in hardness, and therefore are easily abraded and highly sensitive to chemical attack and dissolution. Ceramics, such as silicon nitride ceramics, may also have oxide surfaces. However, unlike their metal counterparts, they are highly resistant to chemical and abrasive action.

Metallic and polymeric devices are also typically hydrophobic. Consequently, bacteria do not have to displace aqueous bodily fluids in order to adhere to the implant's surface. By contrast, ceramics, and silicon nitride in particular, are known to be hydrophilic. For instance, sessile water drop studies demonstrate that silicon nitride has higher wettability than either medical grade titanium or PEEK. This higher wettability is thought to be directly attributable to the hydrophilic surface of silicon nitride based ceramics.

In order for bacteria to adhere to a hydrophilic surface, it must first displace the water that is present on the surface. Therefore, hydrophilic surfaces typically inhibit bacterial adhesion more effectively than do hydrophobic surfaces. It has also been shown that implant surface finish and texture play important roles in bacteria colonization and growth. Irregularities on the surface of typical polymeric or metallic implants tend to promote bacterial adhesion, whereas smooth surfaces tend to inhibit attachment and bio-film formation. This is true because rough surfaces have greater surface area and include depressions that provide favorable sites for colonization.

Counterintuitively, however, certain ceramic materials, including in particular silicon nitride-based ceramic materials, have been demonstrated to not only provide desirable antibacterial properties, but have also been demonstrated to provide further enhanced antibacterial properties with increased, rather than decreased, surface roughness. In other words, silicon nitride surfaces of higher roughness appear to be more resistant to bacterial adhesion than smooth surfaces. This is precisely the opposite of what is observed for many other implant materials, such as Titanium and PEEK. As referenced above and as discussed in greater detail below, compared to medical grade Titanium and PEEK, silicon nitride has been shown to significantly inhibit in vitro bacteria colonization and bio-film formation, and show a much lower live count and live to dead ratio for bacteria during studies. However, in studies between different types of silicon nitride, rough silicon nitride surfaces have been shown to be more effective in inhibiting bacterial colonization (rather than less effective as with most common implant materials) than polished silicon nitride (although both were much more effective in doing so than either Titanium or PEEK).

Various embodiments and implementations will be further understood by the following Examples:

Example 1

In a first working example, the abilities of biomedical implant materials to inhibit bacterial colonization were tested. The study included silicon nitride materials, Biomedical grade 4 Titanium, and PEEK. Four types of bacteria were included in the study: *Staphylococcus epidermidis, Staphylococcus aureus, Pseudomonas aeruginosa, Escherichia coli,* and *Enterococcus.*

Implant samples in the study were sterilized by UV light exposure for 24 hours and surface roughness was characterized using scanning electron microscopy. Bacteria were then inoculated on the surfaces of the samples and incubated for 4, 24, 48, and 72 hours.

Two methods were used to determine bacteria function at the end of each time period: (1) Crystal violet staining; and (2) Live/dead assay. Bacteria were also visually counted using a fluorescence microscope with image analysis software. The experiments were completed in triplicate and repeated three times. Appropriate statistical analyses were then completed using Student t-tests.

For all bacteria, and all incubation times, the silicon nitride samples demonstrated lower bio-film formation, fewer live bacteria, and smaller live to dead bacteria ratios when compared with medical grade Titanium and PEEK. Rough silicon nitride surfaces were even more effective in inhibiting bacterial colonization than polished surfaces. In addition, silicon nitride implants with polished or rough surfaces were both significantly better in inhibition of bacterial colonization than either Titanium or PEEK.

Bio-film formation was also much higher for Titanium and PEEK than for silicon nitride. For example, bio-film formation for *Staphylococcus aureus* on Titanium was three times higher than polished silicon nitride after 72 hours of incubation and more than eight times higher than PEEK after 72 hours of incubation. And the results were even better using relatively rough silicon nitride having a surface roughness of about 1,250 nm Ra. Bio-film formation for *Staphylococcus aureus* on this rougher silicon nitride was less than half of that for the polished silicon nitride after 72 hours.

Live bacteria counts followed similar patterns. Live bacteria counts after 72 hours of incubation were between 1.5× and 30× higher for Titanium and PEEK when compared with silicon nitride. And, again, rough silicon nitride outperformed polished silicon nitride. For example, for *Pseudomonas aeruginosa,* live bacteria count after 72 hours for rough silicon nitride (again, about 1,250 nm Ra) was about one-fifth of that for polished silicon nitride.

Live/dead bacteria ratios were similarly lowest for silicon nitride, and generally lower for rough silicon nitride than for polished silicon nitride. For example, live/dead ratios after 72 hours of incubation for *E. coli* on polished silicon nitride were over three times as high as Titanium and about twice as high as PEEK. For rough silicon nitride, live/dead ratios were about six times as high for Titanium and nearly three times as high for PEEK.

Example 2

In this study, the ability of biomedical implant materials to adsorb common bone-forming proteins was tested. As with Example 1, rough silicon nitride, polished silicon nitride, medical grade Titanium, and PEEK were tested. The proteins tested were fibronectin, vitronectin, and laminin. Enzyme-linked immunosorbent assays (ELISA) were performed for 20 minutes, 1 hour, and 4 hours. Fibronectin, vitronectin, or laminin were directly linked with primary rabbit anti-bovine fibronectin, anti-vitronectin, and anti-laminin, respectively. The amount of each protein adsorbed to the surfaces was measured with an ABTS substrate kit. Light absorbance at 405 nm on a spectro-photometer was analyzed with computer software. ELISA was performed in duplicate and repeated three different times per substrate.

For all incubation times, silicon nitride exhibited significantly greater adsorption of fibronectin and vitronectin when compared with Titanium and PEEK. Silicon nitride also showed greater adsorption of laminin at 1 and 4 hours incubation in comparison to Titanium and PEEK. Rough silicon nitride surfaces (approximately 1,250 nm Ra) were more effective in adsorption of proteins than polished silicon nitride surfaces. However, both silicon nitride surfaces were generally better than either Titanium or PEEK, particularly for fibronectin and vitronectin. Without being limited by theory, it is thought that preferred adsorption of these proteins onto silicon nitride is a probable explanation for its improved bacterial resistance.

Example 3

In this study, in vivo bone formation, inflammation, and infection of various implant materials were studied using a Wistar rat calvaria model. The study considered the strength of bone attachment to these materials. Rough silicon nitride, medical grade Titanium, and PEEK were used in the study.

The study was conducted by implanting sterilized samples into the calvaria of two-year old Wistar rats using standard techniques. Another group of samples was inoculated apriori with *Staphylococcus epidermidis* and implanted into a second group of similar Wistar rats.

The animals were sacrificed at 3, 7, 14, and 90 days. Histology was quantified for the number of macrophages, bacteria, and bio-film proteins surrounding each of the implant materials. In addition, push-out tests were performed to determine bone attachment results and performance.

After 3 days using the non-inoculated samples, the Titanium and PEEK implants were unstable, and thus no histology was able to be performed. The silicon nitride implants (surface roughness of approximately 1,250 nm Ra) exhibited about 3-5% bone-implant interface, as measured using microscopic linear analysis, and about 16-19% new bone growth in the surgical area, as measured using microscopic areal analysis, after 3 days.

After 7 days using the non-inoculated samples, the Titanium and PEEK implants were unstable, and thus no histology was able to be performed. The silicon nitride implants, by contrast, exhibited about 19-21% bone-implant interface and about 28-32% new bone growth in the surgical area after 7 days.

After 14 days using the non-inoculated samples, the Titanium implant exhibited about 7% bone-implant interface and about 11% new bone growth in the surgical area. The PEEK implant exhibited about 2% bone-implant interface and about 14% new bone growth in the surgical area. The silicon nitride implants, by contrast, exhibited about 23-38% bone-implant interface and about 49-51% new bone growth in the surgical area after 14 days.

After 90 days without inoculation, the Titanium and PEEK implants exhibited about 19% and 8% bone-implant interface, respectively, and about 36% and 24% new bone growth, respectively. The silicon nitride implants again performed much better. These implants exhibited a bone-implant interface of about 52-65% and new bone growth of about 66-71%.

With the inoculated samples, all implants were too unstable to perform histology at 3 and 7 days. After 14 days, the Titanium implant exhibited only about 1% bone-implant interface, 75% bacteria-implant interface (measured using microscopic linear analysis), about 9% new bone growth in the surgical area, and about 45% bacterial growth in the surgical area. PEEK exhibited essentially no bone-implant interface, about 2% new bone growth, and about 25% bacterial growth. The bacteria-implant interface with PEEK was unclear. The inoculated silicon nitride implants exhibited a bone-implant interface of about 3-β% after 14 days. New bone growth with the silicon nitride implants was about 25-28%, and bacterial growth was about 11-15%.

After 90 days, the inoculated Titanium implant exhibited about 9% bone-implant interface, about 67% bacteria-implant interface, about 26% new bone growth, and about 21% bacterial growth. The PEEK implant exhibited about 5% bone-implant interface, about 95% bacteria-implant interface, about 21% new bone growth, and about 88% bacterial growth. The inoculated silicon nitride implants exhibited a bone-implant interface of about 21-25% after 90 days. New bone growth with the silicon nitride implants was about 39-42%, and there was no measurable bacterial-implant interface or bacterial growth after 90 days. In fact, there were no bacteria detected on the silicon nitride implants after 90 days.

Push-out strengths were also substantially better with the silicon nitride implants than with either the Titanium or PEEK implants after all implantation times were measured, both with and without inoculation. After 90 days implantation without inoculation, push-out strengths for the silicon nitride implants were more than twice as high as Titanium and more than two-and-a-half times as high as PEEK. With inoculation, silicon nitride push-out strengths were even better compared to Titanium and PEEK for all implantation times. Silicon nitride push-out strengths were more than five times those of either Titanium or PEEK. These results demonstrate substantial bone attachment for silicon nitride when compared to Titanium and PEEK.

Push out strengths were measured by taking a sectioned portion of the calvaria including the implant and cementing the calvaria to wood blocks over a support plate. A load was then applied to the implant and the force required to dislodge the implant from the calvaria was measured.

The histology results further confirm the tested push-out strengths. As discussed above, significantly greater new bone growth was observed in the calvaria defect area for silicon nitride when compared with Titanium and PEEK at all implantation times and under all inoculation conditions.

Example 4

In this study, in vitro assessment of osteoconductivity of various implant materials were studied using a SaOS-2 cell line. The study considered the SaOS-2 cell proliferation on these materials. Silicon nitride filled PEEK (i.e., PEEK filled with 15% α-$Si_3N_4$, β-$Si_3N_4$, and β-SiYAlON powders) and monolithic PEEK substrate materials were used in the study.

The study was conducted by seeding SaOS-2 cells onto squares ($5 \times 10^5$ cells/ml) of each substrate material using standard techniques. After 24 hours, the cells were stained with Blue Hoechst 33342 and counted by fluorescence spectroscopy. Cell seeding was completed after 7 days. The cells were evaluated and counted by fluorescence spectroscopy and the substrate materials were evaluated using laser microscopy, Raman spectroscopy, and scanning electron microscopy (SEM).

Figure 7:
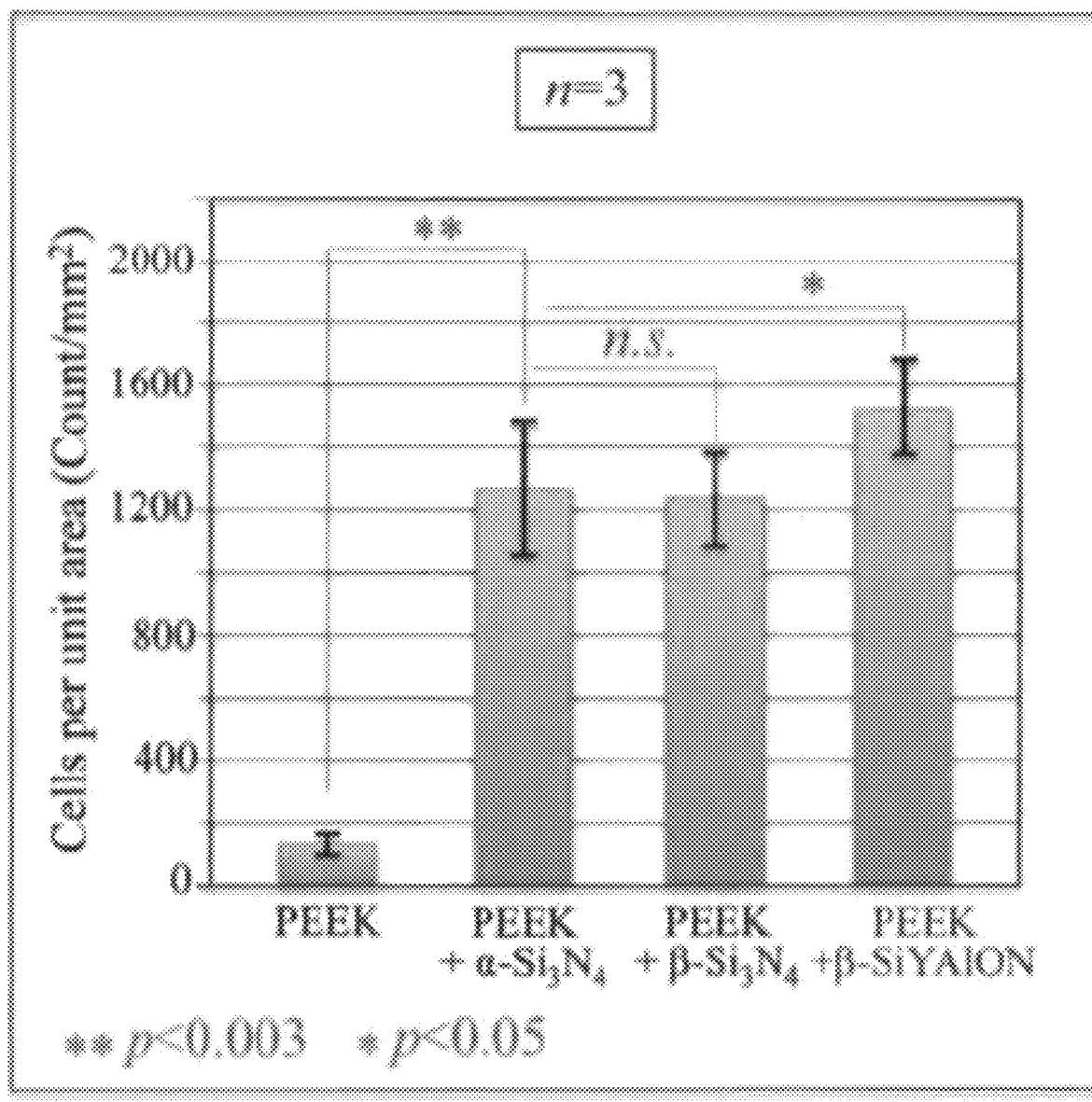
FIG. 7 is a graph of the results of cell counting based on the fluorescence microscopy, according to one aspect of the present disclosure.

FIGS. 6A-6D show fluorescence spectroscopy images of the SaOS-2 cells on the various substrates. FIG. 7 is a graph of the results of cell counting based on the fluorescence microscopy. All composites showed a greater than 600% quicker SaOS-2 cell proliferation in vitro as compared to the monolithic PEEK. The PEEK with 15% β-SiYAlON demonstrated the greatest rate of proliferation with an increase of about 770% over the monolithic PEEK.

Figure 9:
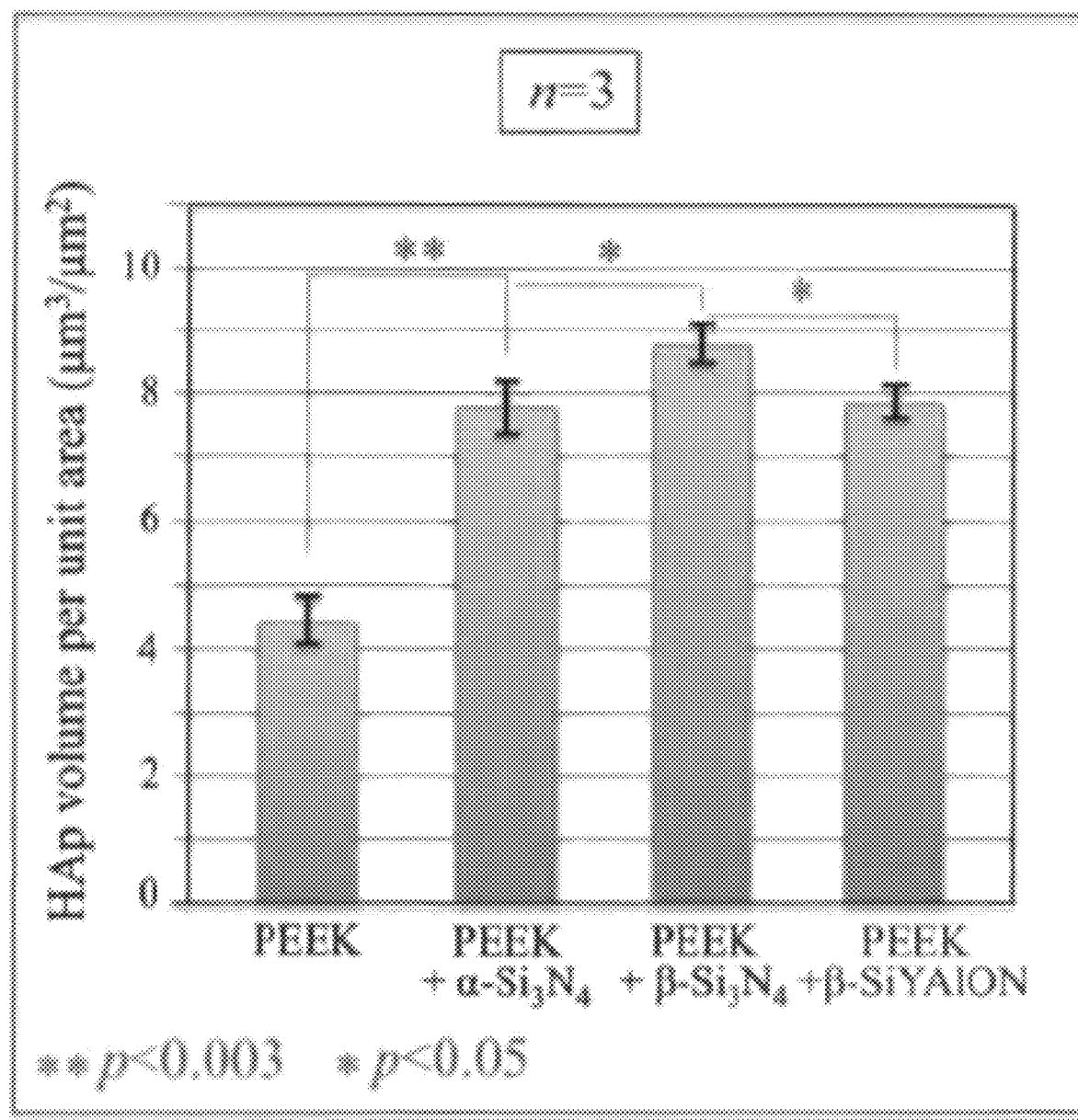
FIG. 9 is a graph of the results of 3D laser microscopy of the substrate materials, showing the bony apatite volume, according to one aspect of the present disclosure.
Figure 10A:
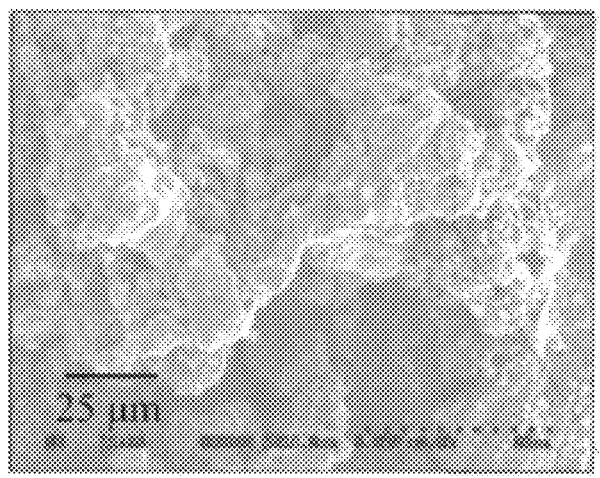
FIG. 10A is a Raman microprobe spectroscopy image of 13-SiYAlON filled PEEK after 7 days of being exposed to SaOS-2 cells.
Figure 10B:
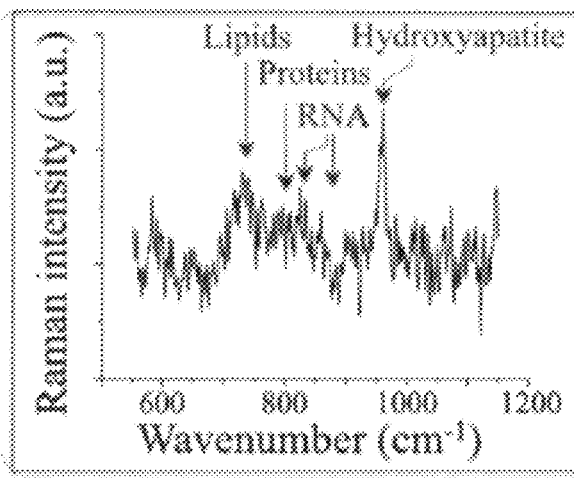
FIG. 10B is graph of Raman intensity of β-SiYAlON filled PEEK after 7 days of being exposed to SaOS-2 cell, according to one aspect of the present disclosure s.

FIGS. 8A-8D show SEM images of the substrate materials before and after exposure to the SaOS-2 cells. FIG. 9 is a graph of the results of 3D laser microscopy of the substrate materials, showing the bony apatite volume. All composites behaved better than monolithic PEEK. PEEK with 15% $Si_3N_4$ exhibited an about 100% increase of in vitro osteoconductivity as compared to monolithic PEEK with SaOS-2 cells. FIGS. 10A and 10B show the results of Raman microprobe spectroscopy on 13-SiYAlON filled PEEK after 7 days of being exposed to SaOS-2 cells. The surface protrusion after 7 days exposure to SaOS-2 cells was confirmed to be bony hydroxyapatite on all the composite samples.

All PEEK composites loaded with 15% $Si_3N_4$ (α- or β) or β-SiYAlON have shown a greatly improved SaOS-2 cell proliferation as compared with monolithic PEEK. All PEEK composites loaded with 15% $Si_3N_4$ (α- or β) or β-SiYAlON have shown significantly improved osteoconductivity with SaOS-2 cell line as compared with monolithic PEEK. The above results were confirmed by several different analytical tools and statistically validated.

Example 5

In this study, in vitro assessment of antibacterial activity of various implant materials were studied using *Staphylococcus epidermidis*. *Staphylococcus epidermidis* (*S. epidermis*) is an important opportunistic pathogen colonizing on human skin inducing high probability of orthopedic device contamination during insertion. Costs related to vascular catheter-related bloodstream infections caused by *S. epidermidis* are about $2 billion per year in US alone. Treatment with antibiotics is complicated by its capability of immune evasion, with high risk of chronic diseases.

The study considered the *S. epidermis* viability on these materials. Silicon nitride filled PEEK (i.e., PEEK filled with 15% α-$Si_3N_4$, β-$Si_3N_4$, and β-SiYAlON powders) and monolithic PEEK substrate materials were used in the study. *S. epidermis* was cultured ($1 \times 10^7$ CFU/ml) and then set in the samples of substrate materials in BHI Agar ($1 \times 10^8$/ml). After 24 hours, the bacteria and samples were assessed by Microbial Viability Assay (WST) and fluorescence spectroscopy by adding DAPI and CFDA and measuring concentration through absorbance at 450 nm.

Figure 12:
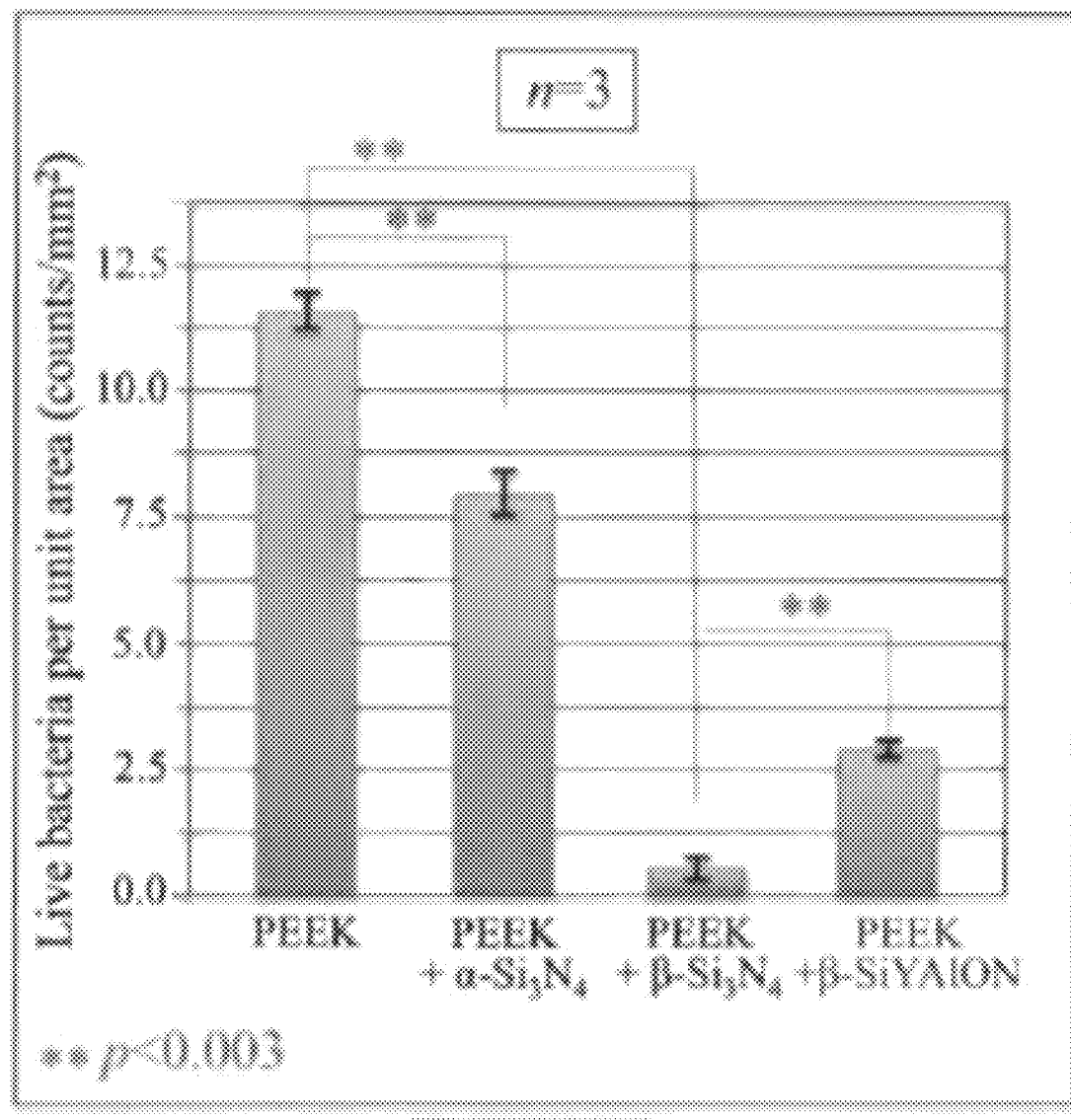
FIG. 12 is a graph of the results of CFDA/DAPI stained positive cells on the various substrates, according to one aspect of the present disclosure, according to one aspect of the present disclosure
Figure 13:
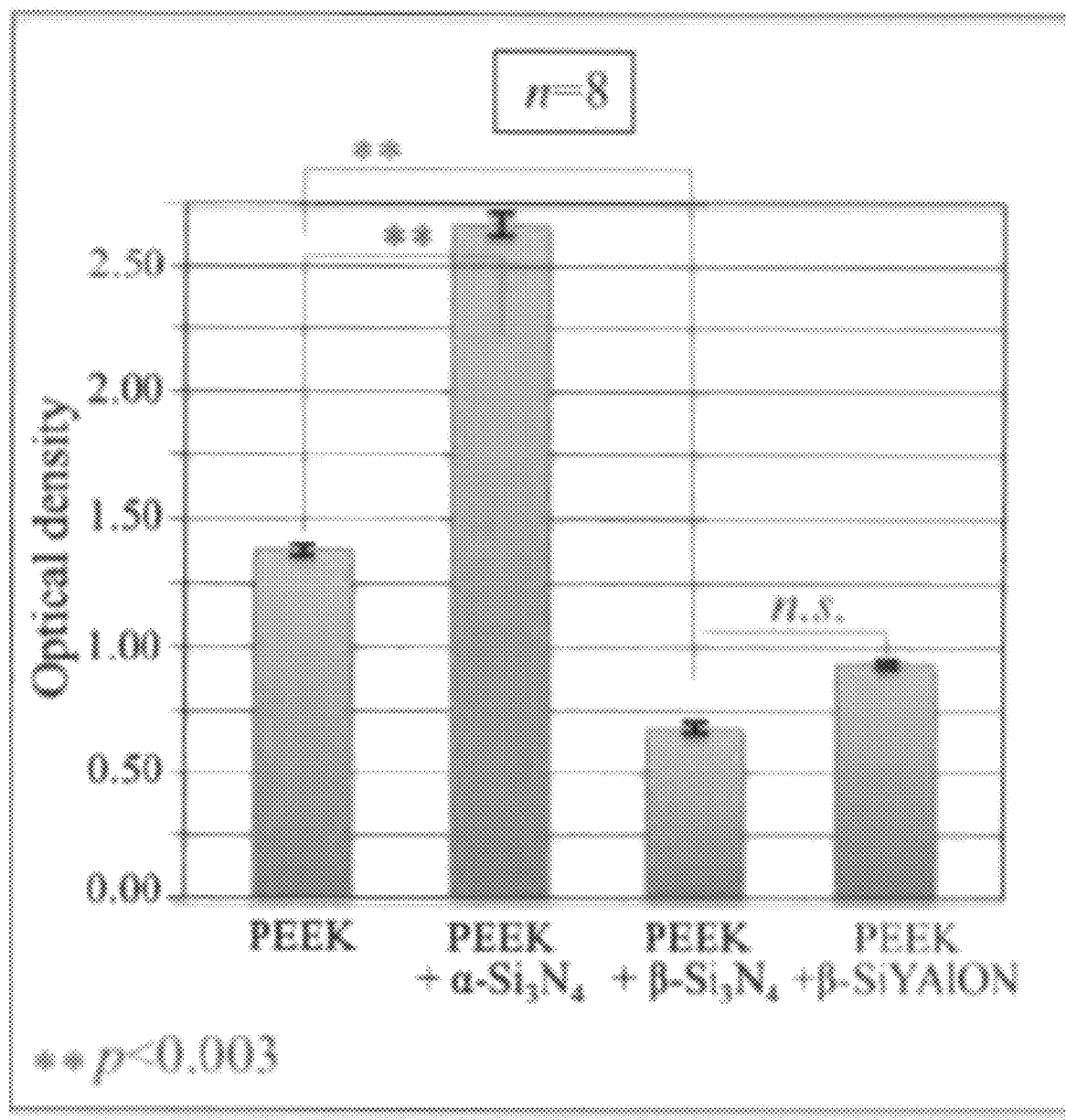
FIG. 13 is a graph of the results of the WST assay (absorbance at 450 nm) for each of the substrates, according to one aspect of the present disclosure.

FIGS. 11A-11D show fluorescence microscopy images with DAPI (nucleus) and CFDA (alive) staining of *S. epidermis* on the various substrates. FIG. 12 is a graph of the results of CFDA/DAPI stained positive cells on the various substrates. PEEK with 15% β-$Si_3N_4$ showed about 1 order of magnitude increase of in vitro antibacterial resistance to *S. epidermis* as compared to monolithic PEEK. FIG. 13 is a graph of the results of the WST assay (absorbance at 450 nm) for each of the substrates. PEEK with 15% β-$Si_3N_4$ showed about a 100% increase of in vitro antibacterial resistance to *S. epidermis* as compared to monolithic PEEK.

PEEK composites loaded with 15% β-$Si_3N_4$ or β-SiYAlON have shown a greatly improved antibacterial resistance as compared with monolithic PEEK. The PEEK composite with 15% α-$Si_3N_4$ did not exhibit the same degree of antibacterial behavior as the other PEEK composites. The above results go clearly beyond a simple rule-of-mixture improvement and show how a relatively low fraction of β-$Si_3N_4$ phase could at least lead to 100% improved antibacterial resistance as compared to monolithic PEEK.

The results in each of the Examples discussed above suggest that, compared to medical grade Titanium and PEEK, silicon nitride results in a substantially better inhibition of in vitro bacterial colonization and bio-film formation, and results in a much lower live to dead ratio for all studied bacteria at all incubation periods. Silicon nitride also demonstrates significantly higher in vitro adsorption of three proteins which may inhibit bacteria growth and promote stem cell differentiation to osteoblasts. This preferential adsorption correlates with, and may be a causative factor in, silicon nitride's ability to decrease bacterial function. Silicon nitride also exhibits enhanced in vivo osteogenesis and osteointegration and demonstrates significant resistance to bacteria compared to monolithic Titanium and PEEK.

The studies discussed in the Examples also tend to suggest that roughened silicon nitride implants generally outperform polished silicon nitride in terms of antibacterial function and/or bone growth and integration. These results suggest not only that monolithic silicon nitride implants and/or or other similar ceramic implants may be surface roughened in order to improve antibacterial function, but also that silicon nitride coatings may be applied to other implants (both silicon nitride and non-silicon nitride, such as metals, polymers, and/or other ceramics). Such coatings may be surface roughened to further improve antibacterial function and provide other desirable characteristics, as discussed above. Preliminary research also tends to indicate that increasing the surface roughness beyond the levels used in the Examples—i.e. about 1,250 nm Ra—may further increase the antibacterial function of the material. For example, in some such embodiments, the surface roughness may be greater than about 1,500 nm Ra. In some such embodiments, the surface roughness may be greater than about 2,000 nm Ra. In some such embodiments, the surface roughness may be greater than about 3,000 nm Ra. In other embodiments, the surface roughness may be between about 500 nm Ra and about 5,000 nm Ra. In some such embodiments, the surface roughness may be between about 1,500 nm Ra and about 5,000 nm Ra. In some such embodiments, the surface roughness may be between about 2,000 nm Ra and about 5,000 nm Ra. In some such embodiments, the surface roughness may be between about 3,000 nm Ra and about 5,000 nm Ra.

Some alternative ceramic materials, such as alumina and zirconia ($ZrO_2$) for example, have certain properties that are similar to those of silicon nitride. As such, it is thought that these ceramic materials, or other similar materials, may exhibit similar antibacterial and osteogenic effects. It is thought that those of ordinary skill in the art, after having had the benefit of this disclosure, may be able to identify such alternative materials. It is also thought that these ceramic materials, or other similar materials, may exhibit improvement in antibacterial function with increased surface roughness, as is the case with silicon nitride ceramics.

Additional embodiments and implementations will be further understood by the following drawings.

FIG. 1A depicts a spinal implant 100. Spinal implant 100 has relatively smooth top, bottom, and side surfaces (102, 104, and 108, respectively). Spinal implant 100 may comprise a silicon nitride ceramic material or another similar ceramic material. Spinal implant 100 also comprises two openings 110 and 112 extending through the top and bottom surfaces of the implant. In some embodiments, spinal implant 100 may comprise a doped silicon nitride material, as described in greater detail above. One or more of the surfaces of spinal implant 100 may be roughened or textured to provide for increased surface area of the silicon nitride material making up the surface(s). For example, one or more surfaces of spinal implant 100 may be roughened or textured by micromachining, grinding, laser etching or texturing, sand or other abrasive blasting, chemical etching, thermal etching, plasma etching, and the like.

FIG. 1B depicts spinal implant 100 after each of the exterior surfaces 102, 104 (surface not visible in the figure), and 108 has been roughened. As explained above, this surface roughening improves the antibacterial function and characteristics of the implant. One or more interior surfaces may also be roughened. For example, interior surfaces 111 and 113 that define openings 110 and 112, respectively, may also be roughened. The extent of roughening of the interior surfaces may be identical to, greater than, or less than, the roughening of exterior surfaces 102, 104, and 108, as desired.

FIG. 1C depicts spinal implant 100 having a plurality of surface features or teeth 114 on the top and bottom surfaces. Surface features 114 may help prevent or at least minimize migration of the implant once positioned within a patient's intervertebral space. Surface features 114 may be formed from the implant 100 before or after the surface roughening has taken place. Similarly, surface features 114 may, alternatively, comprise another material that is attached to the implant 100, again before or after surface roughening.

FIG. 2A depicts an alternative embodiment of a spinal implant 200. Spinal implant 200 may comprise any suitable material or materials, such as metals, polymers, and/or ceramics. Spinal implant 200 also comprises a coating 220. Coating 220 preferably comprises a silicon nitride or doped silicon nitride ceramic material, although it is contemplated that other ceramic materials having certain properties similar to silicon nitride may alternatively be used as a coating. Coating 220 may be applied to any surface exposed or potentially exposed to biological material or activity. For example, in the depicted embodiment, coating 220 is applied to top surface 202, bottom surface 204, side surface 208, and to interior surfaces 211 and 213 that define openings 210 and 212, respectively. Coating 220 may be applied to take advantage of the unique antibacterial properties and characteristics of silicon nitride discussed elsewhere herein. In some embodiments, the coating thickness can range from between about 5 nanometers up to about 5 millimeters. In some preferred embodiments, the coating thickness may be between about 1 micrometer and about 125 micrometers.

For example, because PEEK, which is very common in spinal implants, performs very poorly in a bacterial environment, silicon nitride ceramic coatings or layers (or another similar material) may be applied to a PEEK spinal implant to improve the antibacterial function of the implant and/or to provide other advantages as discussed in greater detail above. The coating(s) may be applied by any suitable methodology known to those of ordinary skill in the art, such as chemical vapor deposition (CVD), physical vapor deposition (PVD), plasma spraying, electro-deposition or electrophoretic deposition, slurry coating and/or high-temperature diffusion.

To further enhance the antibacterial characteristics of the implant, the coating 220, or one or more portions of the coating 220, may be surface roughened, as illustrated in FIG. 2B. The coating surface roughening may be applied to any and all portions of the implant that are or could be exposed to biological activity or material. For example, in the embodiment depicted in FIG. 2B, each of surfaces 202, 204, 208, 211, and 213 have been roughened or textured as described above. In some embodiments, the surface of the implant may be roughened or textured before the coating is applied, either in lieu of, or in addition to surface roughening or texturing on the coating.

The principles, materials, and methods described herein may also be applied to other biomedical implants. For example, FIGS. 3A-3B and 4A-4B illustrate a hip implant 300 comprising a femoral stem 330 that is configured to be received within a patient's femur, a neck 340, and a modular acetabular head 350 configured to receive a ball joint (not shown) that will ultimately be positioned in an acetabular cup, or within a patient's natural acetabulum.

One or more coatings 320 may be applied to the femoral stem 330 of hip implant 300, as shown in FIG. 3A. In preferred embodiments, coating 320 comprises a silicon nitride ceramic material. In alternative embodiments, other portions of the implant may also be coated with a silicon nitride ceramic or another similar material. For example, coating 320 may also be applied to femoral stem 330, neck 340, and/or modular acetabular head 350, as desired.

Figure 3B:
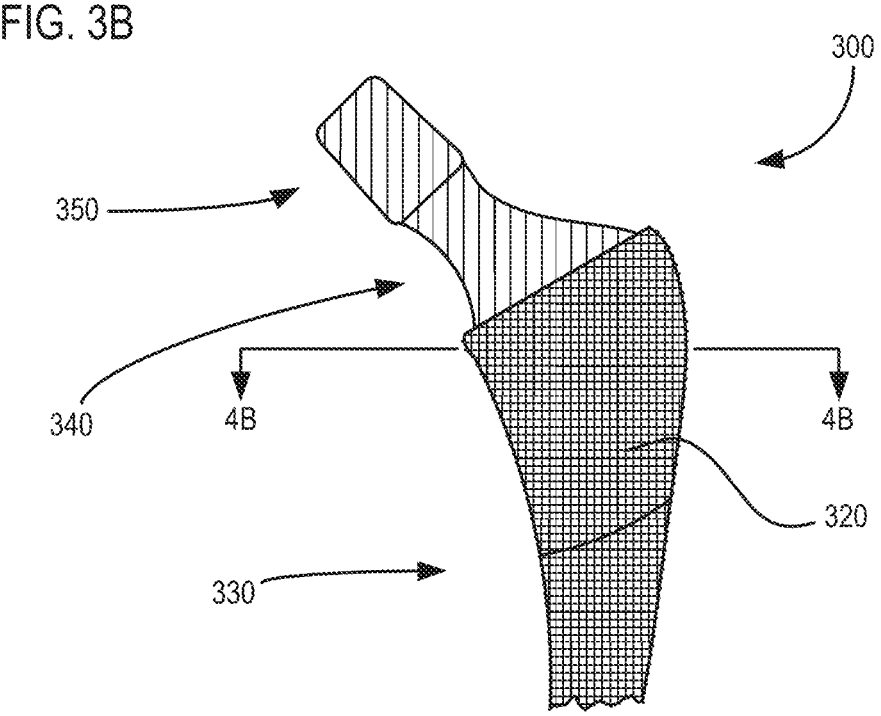
FIG. 3B is a perspective view of the embodiment of FIG. 3A after a surface roughening process has been applied to the coating of the implant, according to one aspect of the present disclosure.

In order to further enhance the antibacterial properties of the implant 300, one or more surfaces/portions of the implant 300 may be roughened and/or textured. For example, as shown in FIG. 3B, femoral stem 330, which comprises coating 320, may be roughened and/or textured after coating 320 has been applied. Alternatively, femoral stem 330 and/or any other desired region of implant 300 (or any of the other implants discussed herein) may be roughened and/or textured before coating 320 has been applied. As yet another alternative, one or more surfaces of the implant may be textured and/or roughened both before and after the antibacterial coating has been applied.

Figure 4A:
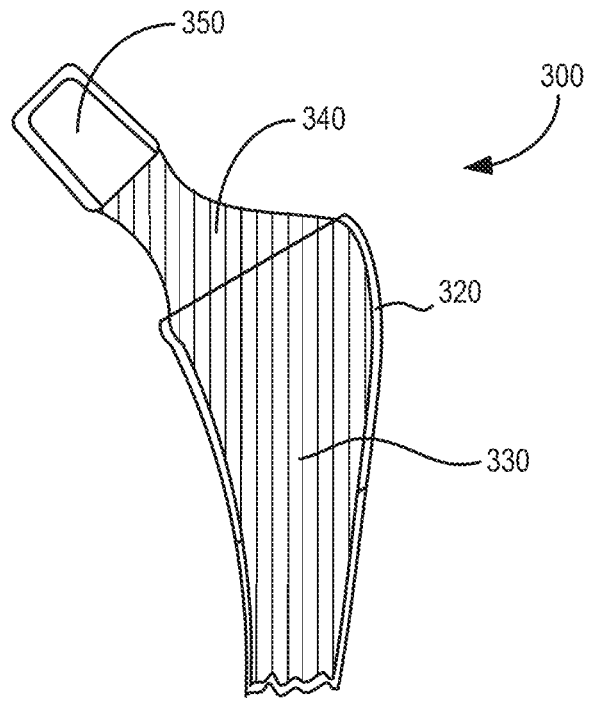
FIG. 4A is a cross-sectional view taken along line 4A-4A in FIG. 3A.

FIG. 4A is a cross-sectional view taken along line 4A-4A in FIG. 3A. As shown in this figure, coating 320 extends only along the femoral stem 330 portion of implant 300. However, as discussed above, in alternative embodiments, coating 320 may be applied to other portions of the implant as well (in some embodiments, the coating may be applied to the entire implant).

Figure 4B:
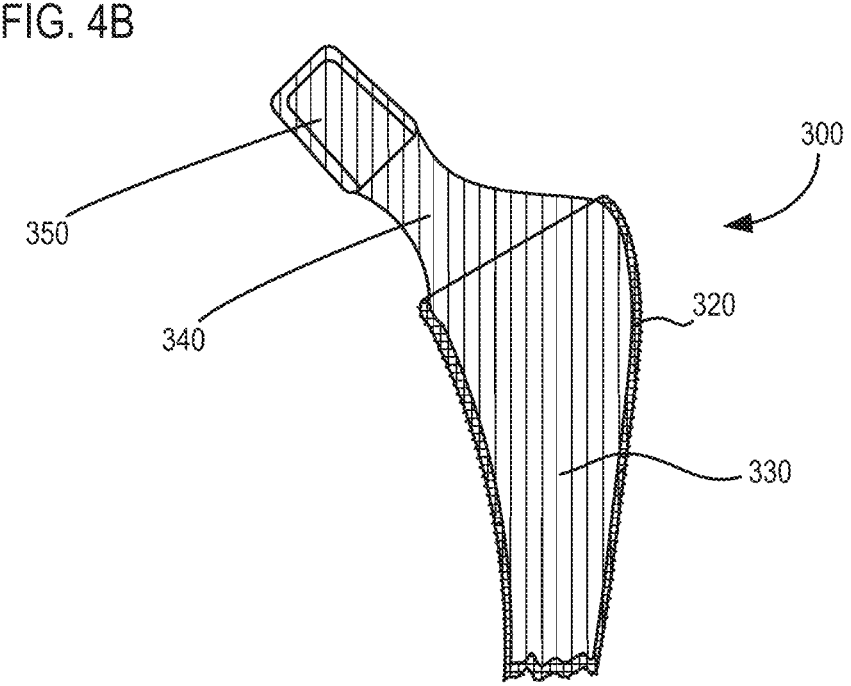
FIG. 4B is a cross-sectional view taken along line 4B-4B in FIG. 3B.

FIG. 4B is a cross-sectional view taken along line 4B-4B in FIG. 3B. This figure illustrates the surface of the femoral stem 330 of implant 300 after the roughening/texturing process has been completed.

Figure 5A:
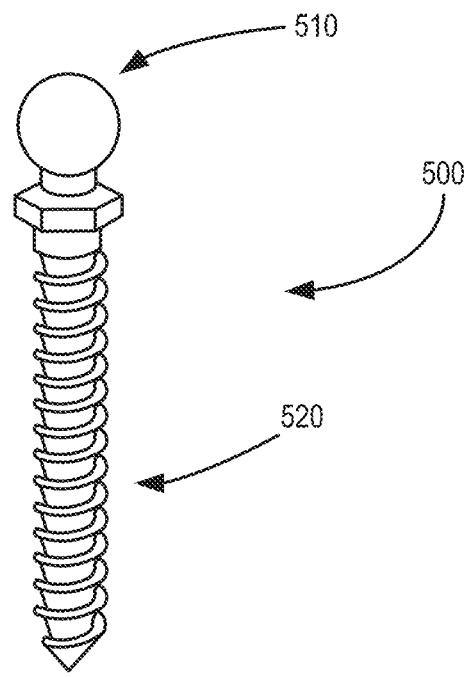
FIG. 5A is a perspective view of an embodiment of a bone screw implant.
Figure 5B:
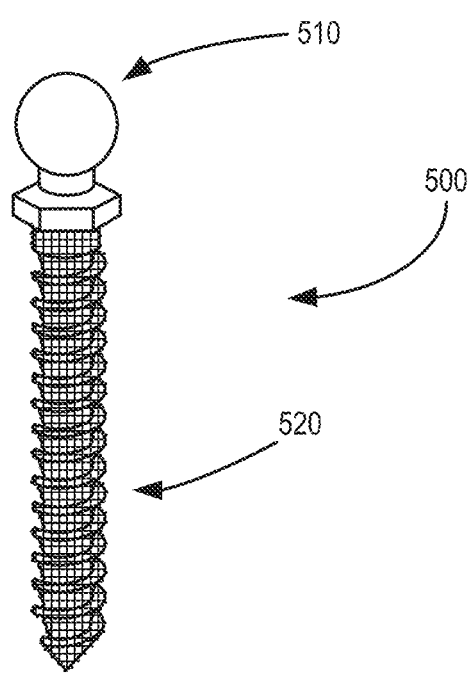
FIG. 5B is a perspective view of the embodiment of FIG. 5A after a surface roughening process has been applied to the implant, according to one aspect of the present disclosure.

Still other alternative embodiments are depicted in FIGS. 5A and 5B. These figures illustrate a bone screw 500. Bone screw 500 may comprise a pedicle screw, for example. Bone screw 500 comprises a spherical head 510 and a threaded shaft 520. Bone screw 500, or one or more portions of bone screw 500, may comprise a silicon nitride ceramic material. One or more portions or surfaces of bone screw 500 may also be roughened or textured to improve antibacterial or other characteristics of the implant. For example, as shown in FIG. 5B, threaded shaft 520 has been roughened. Head 510 of screw 500 may remain smooth, or may be polished smooth, to provide for desired articulation within a spinal fixation system connector. However, for other embodiments, it may be desirable to roughen the surface of head 510 as well. This may provide for not only the improved antibacterial characteristics discussed herein, but may also provide a desirable friction interface with another component of a spinal fixation system.

In other embodiments, bone screw 500, or any of the other embodiments disclosed herein, may comprise another suitable material, such as Titanium. In such embodiments, a silicon nitride coating may be applied to the implant rather than forming the entire implant from a silicon nitride material. As disclosed above, the coating and/or the undersurface of the coating (i.e., the surface of the original implant itself) may be roughened or textured to further improve antibacterial and other characteristics.

In still other embodiments, bone screw 500, or any of the other embodiments disclosed herein, may comprise a biomedical material, such as a metal, ceramic, or polymer that includes a silicon nitride filler, or that otherwise incorporate a silicon nitride material into the material used to form the implant. For example, silicon nitride may be used as a filler or otherwise incorporated into polymers, such as poly-ether-ether-ketone (PEEK), poly(methylmethacrylate), poly(ethyleneterephthalate), poly(dimethylsiloxane), poly(tetrafluoroethylene), polyethylene, and/or polyurethane. Silicon nitride may also be used as a filler otherwise incorporated into other materials used to form other biomedical implants, such as metals, including Titanium, Silver, Nitinol, Platinum, Copper, and related alloys, for example. As still another alternative, silicon nitride may be used as a filler or otherwise incorporated into other materials, such as ceramics and cermets. By incorporating silicon nitride into other materials, it is expected that some of the antibacterial advantages and/or other advantageous properties described herein may be realized. Silicon nitride may also be incorporated into another materials used as part of one or more of the coatings described herein to increase antibacterial function.

It will be understood by those having skill in the art that changes may be made to the details of the above-described embodiments without departing from the underlying principles presented herein. For example, any suitable combination of various embodiments, or the features thereof, is contemplated.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

Throughout this specification, any reference to "one embodiment," "an embodiment," or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, inventive aspects lie in a combination of fewer than all features of any single foregoing disclosed embodiment. It will be apparent to those having skill in the art that changes may be made to the details of the above-described embodiments without departing from the underlying principles set forth herein. The scope of the present invention should, therefore, be determined only by the following claims.

The invention claimed is:

1. A method for improving the antibacterial characteristics of a biomedical implant, the method comprising the steps of:
   providing a biomedical implant comprising a poly-ether-ether-ketone (PEEK) and/or titanium substrate material; and
   applying a coating of SiYAlON on the biomedical implant by chemical vapor deposition (CVD), physical vapor deposition (PVD), plasma spraying, electro-deposition, electrophoretic deposition, slurry coating, or high-temperature diffusion, wherein the SiYAlON coating has a thickness of 1 µm to 125 µm.

2. The method of claim 1, wherein the SiYAlON is β-SiYAlON.

3. The method of claim 1, wherein the coated biomedical implant has increased bacterial resistance as compared to the substrate material alone.

4. The method of claim 1, wherein the biomedical implant comprises an intervertebral spinal implant.

5. The method of claim 1, wherein the biomedical implant comprises PEEK.

6. The method of claim 1, wherein the biomedical implant comprises titanium.

7. A biomedical implant with improved antibacterial characteristics comprising:
   a poly-ether-ether-ketone (PEEK) and/or titanium substrate material; and
   a coating on the substrate material comprising β-SiYAlON, wherein the coating has a thickness of 1 µm to 125 µm,
   wherein the coating is applied to the substrate material by chemical vapor deposition (CVD), physical vapor deposition (PVD), plasma spraying, electro-deposition, electrophoretic deposition, slurry coating, or high-temperature diffusion.

8. The biomedical implant of claim 7, wherein the biomedical implant has increased bacterial resistance as compared to the substrate material alone.

9. The biomedical implant of claim 7, wherein the substrate material comprises PEEK.

10. The biomedical implant of claim 7, wherein the substrate material comprises titanium.

11. The biomedical implant of claim 7, wherein the biomedical implant is selected from an intervertebral spinal implant, a hip implant, an orthopedic plate, or a bone screw.

12. The biomedical implant of claim 7, wherein the biomedical implant comprises a titanium bone screw.

13. A biomedical implant with improved antibacterial characteristics comprising:
   a polymeric substrate material filled with about 10 vol. % to about 20 vol. % of a powder comprising β-SiYAlON wherein the biomedical implant is selected from an intervertebral spinal implant, a hip implant, an orthopedic plate, or a bone screw.

14. The biomedical implant of claim 13, wherein the substrate material comprises poly-ether-ether-ketone (PEEK).

* * * * *